(12) United States Patent
Nakajima et al.

(10) Patent No.: US 10,098,608 B2
(45) Date of Patent: *Oct. 16, 2018

(54) INFORMATION PROCESSING APPARATUS FOR CALCULATING INDEX FOR SUPPORTING DIAGNOSIS OF SUBJECT

(71) Applicant: Fujifilm RI Pharma Co., Ltd., Chuo-ku (JP)

(72) Inventors: Kenichi Nakajima, Kanazawa (JP); Koichi Okuda, Matsusaka (JP); Tetsuo Hosoya, Chuo-ku (JP); Yumiko Kirihara, Chuo-Ku (JP); Takehiro Ishikawa, Chuo-ku (JP)

(73) Assignee: Fujifilm RI Pharma Co., Ltd., Chuo-ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/786,484

(22) PCT Filed: Apr. 25, 2014

(86) PCT No.: PCT/JP2014/061692
§ 371 (c)(1),
(2) Date: Oct. 22, 2015

(87) PCT Pub. No.: WO2014/175421
PCT Pub. Date: Oct. 30, 2014

(65) Prior Publication Data
US 2016/0066878 A1    Mar. 10, 2016

(30) Foreign Application Priority Data

Apr. 26, 2013  (JP) .................................. 2013-094074

(51) Int. Cl.
G06K 9/00    (2006.01)
A61B 6/00    (2006.01)
(Continued)

(52) U.S. Cl.
CPC .............. *A61B 6/583* (2013.01); *A61B 6/037* (2013.01); *A61B 6/4258* (2013.01); *A61B 6/469* (2013.01);
(Continued)

(58) Field of Classification Search
None
See application file for complete search history.

(56) References Cited

U.S. PATENT DOCUMENTS 6,694,047 B1    2/2004  Farrokhnia et al.
7,324,673 B1 *  1/2008  Yamanaka .............. G06T 5/009
                                                     358/520
(Continued)

FOREIGN PATENT DOCUMENTS

JP    2001-054514    2/2001
JP    2012-078088    4/2012
(Continued)

OTHER PUBLICATIONS

Nakajima et al "Standardization of metaiodobenzylguanidine heart to mediastinum ratio using a calibration phantom: effects of correction on normal databases and a multicentre study", Eur J Nucl Med Mol Imaging (2012) 39:113-119.*

(Continued)

*Primary Examiner* — Shervin Nakhjavan
(74) *Attorney, Agent, or Firm* — Schwegman Lundberg & Woessner, P.A.

(57) ABSTRACT

An object is to more accurately compare diagnosis indexes with each other, which are calculated from data obtained in different environments with a cardiac-function diagnostic medicine. A conversion function calculation unit acquires a first phantom Heart/Mediastinum ratio (H/M ratio) and a second phantom H/M ratio based on a phantom, the first phantom H/M ratio that is an H/M ratio of the phantom in (Continued)

the first imaging environment being acquired by performing, based on phantom data that is data of a first phantom image obtained by imaging the phantom in the first imaging environment and digital phantom data that is data of a digital phantom including a cardiac ROI and a mediastinum ROI, positioning of the digital phantom on the first phantom image, and by calculating based on the phantom data of the first phantom image to which the cardiac ROI and the mediastinum ROI are set; and obtains a conversion function based on the first phantom H/M ratio and the second phantom H/M ratio.

20 Claims, 15 Drawing Sheets

(51) Int. Cl.
| | | |
|---|---|---|
| *A61B 6/03* | (2006.01) | |
| *G06F 19/00* | (2018.01) | |
| *A61K 51/04* | (2006.01) | |
| *G16H 50/20* | (2018.01) | |
| *A61B 8/08* | (2006.01) | |
| *G16H 50/30* | (2018.01) | |

(52) U.S. Cl.
CPC ............. *A61B 6/481* (2013.01); *A61B 6/503* (2013.01); *A61B 6/5211* (2013.01); *A61B 6/5217* (2013.01); *A61K 51/0406* (2013.01); *G06F 19/00* (2013.01); *G06F 19/321* (2013.01); *G16H 50/20* (2018.01); *A61B 6/5294* (2013.01); *A61B 8/0883* (2013.01); *G16H 50/30* (2018.01)

(56) References Cited

U.S. PATENT DOCUMENTS

| | | | | |
|---|---|---|---|---|
| 2013/0324843 | A1* | 12/2013 | Peretz | A61B 6/037 600/431 |
| 2016/0073990 | A1* | 3/2016 | Nakajima | A61B 6/037 600/431 |

FOREIGN PATENT DOCUMENTS

| | | |
|---|---|---|
| WO | WO-2014/175421 | 10/2014 |
| WO | WO-2014175422 | 10/2014 |

OTHER PUBLICATIONS

Inoue et al "Acquisition Protocols and Correction Methods for Estimation of the Heart-to-Mediastinum Ratio in 123I-Metaiodobenzylguanidine Cardiac Sympathetic Imaging",Received Jul. 27, 2012; revision accepted Nov. 26, 2012. For correspondence or reprints contact: Yusuke Inoue, Department of Diagnostic Radiology, Kitasato University School of Medi.*
Verberne et al "Influence of collimator choice and simulated clinical conditions on 123I-MIBG heart/mediastinum ratios: a phantom study", Eur J Nucl Med Mol Imaging (2005) 32:1100-1107.*
"Guidelines for Clinical Use of Cardiac Nuclear Medicine (JCS 2010)", *JCS Joint Working Group, Circulation Journal*, 76, (2012), 761-767.
"Guidelines for Diagnosis and Treatment of Circulatory Diseases (2003-2004 Joint Working Groups Report)", Guidelines for Clinical Use of Cardiac Nuclear Medicine (JCS 2005), The Japanese Circulation Society, 78 pgs.
"International Application No. PCT/JP2014/061692, International Preliminary Report on Patentability dated Oct. 27, 2015", (w/ English Translation), 11 pgs.
"International Application No. PCT/JP2014/061692, Written Opinion dated Aug. 12, 2014", (w/ English Translation), 9 pgs.
Fukuyama, Naoya, "Clinical evaluation on sympathetic nerve activity—Imaging sympathetic nerve of heart disease patient with MIBG-", *Heart View*, 14(8), (2010), 14-20.
Hasegawa, Daisuke, "123I-MIBG Shin Jukaku Hi Sanshutsu ni Okeru Han Jidoka Soft no Kensho-Okayama-Ken Tashisetsu Kyodo Kenkyu", [online]. Chugoku-Shikoku Forum for Radiological Technology (CSFRT 2012). [retrieved on Jul. 23, 2014]. Retrieved from the Internet: <URL: http://csfrt8th.umin.jp/img/atoshoroku/pdf/csfrt2012.pdf>, (2012), p. 150.
Nakajima, Kenichi, "MIBG test and measurement method", Medical View Co., Ltd., (2002), 34-42.
Nakajima, Kenichi, et al., "Standardization of metaiodobenzylguanidine heart to mediastinum ratio using a calibration phantom: effects of correction on normal databases and a multicentre study", *Eur J Nucl Med Mol Imaging*, 39, (2012), 113-119.
Taki, Junichi, "MIBG scintigraphy in neurological disease scintigraphy disease", *Neurology*, 64(6), (2006), 585-592.
Yokoyama, Tsuyoshi, "123I-MIBG Shin Jukaku Hi (H/M) no Sochikan no Hyojunka: Phantom ni yoru Kosei to Rinshorei deno Kensho", *Japanese Journal of Nuclear Medicine*, 49(3), (2012), p. 262.
"International Application No. PCT/JP2014/061692, International Search Report dated Aug. 12, 2014", (Aug. 12, 2014), 5 pgs.
"U.S. Appl. No. 14/786,488, Non Final Office Action dated Mar. 30, 2018", 33 pgs.
"International Application No. PCT/JP2014/061693, International Search Report dated Aug. 12, 2014", (Aug. 12, 2014), 4 pgs.
Agostini, D., et al., "I-123-mIBG myocardial imaging for assessment of risk for a major cardiac event in heart failure patients: insights from a retrospective European multicenter study", Eur. J. Nucl. Med. Mol. Imaging 35(3), (2008), 535-546.
Jacobson, et al., J. Am. Coll. Cardiol. 55, (2010), 2212-2221.
Jacobson, Arnold F., et al., "123I-mIBG Scintigraphy to predict risk for adverse cardiac outcomes in heart failure patients: Design of two prospective multicenter international trials", J. Nucl. Cardiol. 16(1), (2009), 113-121.
Januzzi, James L., et al., "NT-proBNP testing for diagnosis and short-term prognosis in acute destabilized heart failure: an international pooled analysis of 1256 patients: The International Collaborative of NT-proBNP Study", European Heart Journal 27(3), (2006), 330-337.
Nakajima, Kenichi, et al., "Correction of iodine-123-labeled metaiodobenzylguanidine uptake with multi-window methods for standardization of the heart-to-mediastinum ratio", J. Nucl. Cardiol. 14(6), (2007), 843-851.
"U.S. Appl. No. 14/786,488, Response filed Jul. 26, 2018 to Non Final Office Action dated Mar. 30, 2018", 14 pgs.

* cited by examiner

5 year mortality risk for heart failure

| Gender | ● Male  ○ Female | ☐ Correction |
| NYHA class | ○ 1-2  ● 3-4 | |
| H/M R | 1.9 | |
| Age | 60 | |
| LVEF | 42 | |

5 year mortality risk: 25 %/5y

Calc (B)

5 year mortality risk for heart failure

| Gender | ● Male  ○ Female | ☑ Correction |
| NYHA class | ○ 1-2  ● 3-4 | |
| H/M R | 1.9 | |
| Age | 60 | |
| LVEF | 42 | |

5 year mortality risk: 35 %/5y

Calc

INFORMATION PROCESSING APPARATUS FOR CALCULATING INDEX FOR SUPPORTING DIAGNOSIS OF SUBJECT

PRIORITY CLAIM TO RELATED APPLICATIONS

This application is a U.S. national stage application filed under 35 U.S.C. § 371 from International Application Serial No. PCT/JP2014/061692, which was filed 25 Apr. 2014, and published as WO2014/175421 on 30 Oct. 2014, and which claims priority to Japanese Application No. 2013-094074, filed 26 Apr. 2013, which applications and publication are incorporated by reference as if reproduced herein and made a part hereof in their entirety, and the benefit of priority of each of which is claimed herein.

TECHNICAL FIELD

This invention relates to a technique of standardizing indexes for supporting a diagnosis of a subject, and for example, relates to an information processing technique that makes indexes, calculated from pieces of data acquired in difference environments, capable of being compared with each other.

BACKGROUND ART

Indexes for diagnosis support have been calculated by administering a diagnostic medicine (cardiac function diagnostic medicine) for diagnosing a cardiac function to a subject and analyzing an image obtained by imaging the subject. Examples of the diagnostic medicines include a radioactive medicine that accumulates in myocardium by nature (hereinafter, also referred to as a radio isotope (RI) medicine). Examples of the RI medicine include MIBG (3-iodobenzylguanidine), MIBI (technetium hexakis-2-methoxyisobutylisonitrile), and thallium chloride. For example, an index known as heart/mediastinum ratio (H/M ratio) can be obtained from an RI planer image obtained by detecting radioactivity from a subject administered with MIBG. The H/M ratio is obtained from a comparison between an average count value in the cardiac region and an average count value in the mediastinum region. The H/M ratio is used for diagnosis as well as evaluation of severity and prognosis for a subject with a cardiac disease (NPL 1 to NPL 3). The H/M ratio is also used for a nerve disease, to diagnose dementia with Lewy bodies (NPL 4).

MIBI is used to evaluate a myocardial lesion in cardiac diseases such as ischemic cardiac disease, heart failure, and cardiac sarcoidosis, by measuring a washout amount. In such a case, a myocardium washout rate (WR) indicating a rate of the RI medicine washed out from the myocardium is used as the index. The WR is obtained from count values in an early image captured in a first time period after the RI medicine is administered and count values in a late image captured in a second time period later than the first time period. For example, the H/M ratio may also be used for measuring an uptake amount of other radioactive medicines such as thallium chloride into the myocardium.

PTL 1 discloses a technique of preventing a difference from occurring among practitioners in the calculated H/M ratios.

Furthermore, a technique has been known that is effective when the H/M ratios respectively calculated from RI planer images captured in different imaging environments. More specifically, the difference between the H/M ratios due to the difference between the imaging environments is eliminated, so that the H/M ratios respectively calculated from RI planer images captured under different imaging environments can be compared with each other (NPL 5).

CITATION LIST

Patent Literature

[PTL 1]
Japanese Patent Application Publication No. 2012-78088

Non Patent Literature

[NPL 1]
The Japanese circulation society, Guidelines for Diagnosis and Treatment of circulatory diseases (2003-2004 Joint Working Groups Report) "Guidelines for Clinical Use of Cardiac Nuclear Medicine", Circulation Journal Vol. 69, Suppl. IV, 1125 to 1202, 2006
[NPL 2]
Heart failure and sympathetic nerve function, Image diagnosis from pathophysiology to prognostic evaluation "MIBG test and measurement method", Kenichi Nakajima, 34 to 42, 2002, MEDICAL VIEW CO., LTD.
[NPL 3]
Clinical evaluation on sympathetic nerve activity—Imaging sympathetic nerve of heart disease patient with MIBG—, Naoya Fukuyama, Heart View, 14(8) 14 to 20, 2010
[NPL 4]
Feature article: MIBG myocardial scintigraphy and neurological disease "MIBG scintigraphy in neurological disease scintigraphy" Junichi Taki, neurology, 64(6): 585 to 592, 2006
[NPL 5]
Standardization of metaiodobenzylguanidine heart to mediastinum ratio using a calibration phantom: effects of correction on normal database and a multicentre study, Kenichi Nakajima et al, Eur J Nucl Med Mol Imaging (2012) 39: 113 to 119

SUMMARY OF INVENTION

Technical Problem

With the technique described in NPL 5, the H/M ratios respectively calculated from the RI planer images captured in different imaging environments. More specifically, in the technique described in NPL 5, a function (regression formula) for converting an H/M ratio obtained from a certain imaging environment into an H/M ratio to be obtained from another imaging environment, and thus the H/M ratios can be compared with each other with the function.

An object of this invention is to more accurately compare H/M ratios, respectively calculated from images captured in different imaging environments, with each other.

Solution to Problem

A storage medium according to one aspect of this invention is a computer-readable storage medium storing a program causing a computer to execute processing of: acquiring a first phantom Heart/Mediastinum ratio (H/M ratio) and a second phantom H/M ratio based on a phantom, the first phantom H/M ratio that is an H/M ratio of the phantom in the first imaging environment being acquired by performing, based on phantom data that is data of a first phantom image obtained by imaging the phantom in the first imaging environment and digital phantom data that is data of a digital phantom including a cardiac ROI and a mediastinum ROI, positioning of the digital phantom on the first phantom image, and by calculating based on the phantom data of the first phantom image to which the cardiac ROI and the mediastinum ROI are set; and obtaining a conversion function based on the first phantom H/M ratio and the second phantom H/M ratio.

A storage medium according to another aspect of this invention is a computer-readable storage medium storing a program causing a computer to execute processing of: acquiring a conversion function obtained based on a first phantom Heart/Mediastinum ratio (H/M ratio) and a second phantom H/M ratio based on a phantom, the first phantom H/M ratio that is an H/M ratio of the phantom in the first imaging environment being acquired by performing, based on phantom data that is data of a first phantom image obtained by imaging the phantom in the first imaging environment and digital phantom data that is data of a digital phantom including a cardiac ROI and a mediastinum ROI, positioning of the digital phantom on the first phantom image, and by calculating based on the phantom data of the first phantom image to which the cardiac ROI and the mediastinum ROI are set; and converting an H/M ratio related to a subject by using the conversion function.

An information processing apparatus according to one aspect of this invention includes: an acquisition unit that acquires a first phantom Heart/Mediastinum ratio (H/M ratio) and a second phantom H/M ratio based on a phantom, the first phantom H/M ratio that is an H/M ratio of the phantom in the first imaging environment being acquired by performing, based on phantom data that is data of a first phantom image obtained by imaging the phantom in the first imaging environment and digital phantom data that is data of a digital phantom including a cardiac ROI and a mediastinum ROI, positioning of the digital phantom on the first phantom image, and by calculating based on the phantom data of the first phantom image to which the cardiac ROI and the mediastinum ROI are set; and a conversion function calculation unit that calculates a conversion function based on the first phantom H/M ratio and the second phantom H/M ratio.

An information processing apparatus according to another aspect of this invention includes: an acquisition unit that acquires a conversion function obtained based on a first phantom Heart/Mediastinum ratio (H/M ratio) and a second phantom H/M ratio based on a phantom, the first phantom H/M ratio that is an H/M ratio of the phantom in the first imaging environment being acquired by performing, based on phantom data that is data of a first phantom image obtained by imaging the phantom in the first imaging environment and digital phantom data that is data of a digital phantom including a cardiac ROI and a mediastinum ROI, positioning of the digital phantom on the first phantom image, and by calculating based on the phantom data of the first phantom image to which the cardiac ROI and the mediastinum ROI are set; and a conversion unit that converts an H/M ratio related to a subject by using the conversion function.

BRIEF DESCRIPTION OF DRAWINGS

FIG. 15 illustrates a data input window 90.

DESCRIPTION OF EMBODIMENTS

An information processing apparatus according to a first embodiment of the present invention is described below with reference to the figures.

The information processing apparatus according to the present embodiment executes processing of making it possible to compare H/M ratios as diagnosis indexes respectively calculated from images captured in different imaging environments with each other.

In the present embodiment, a planer image of a subject, administered with a cardiac function diagnostic medicine, captured in a certain imaging environment including a predetermined imaging device and a planer image obtained by capturing an image of a phantom containing the same medicine are used. In cases described in the following embodiments, MIBG ($^{123}$I-3-iodobenzylguanidine) is used as the cardiac function diagnostic medicine.

Figure 1:
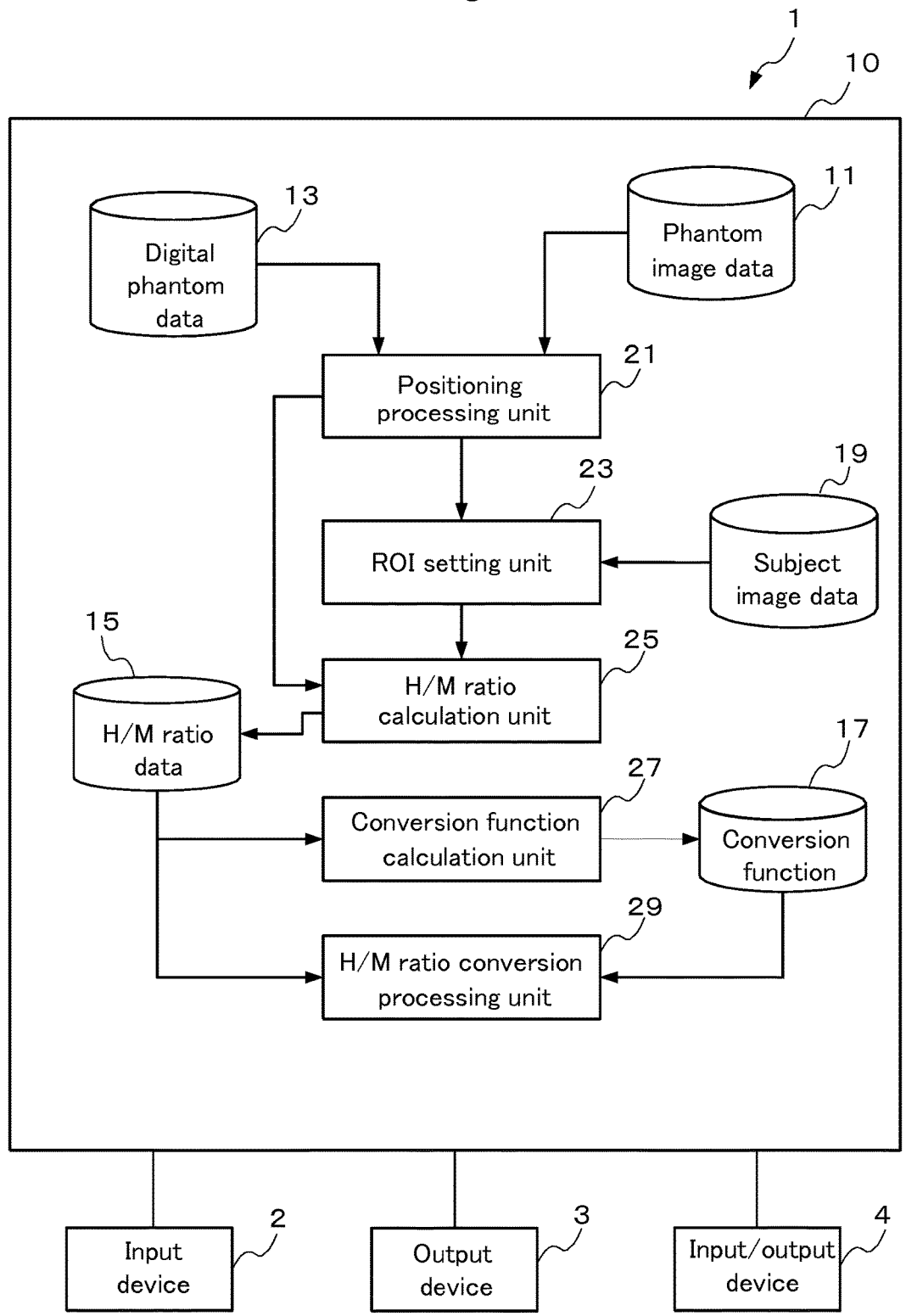
FIG. 1 illustrates an overall configuration of an information processing apparatus 1 according to the present embodiment.

FIG. 1 illustrates an overall configuration of an information processing apparatus 1 according to the present embodiment. As illustrated in the figure, in the information processing apparatus 1, at least one of an input device 2, an output device 3, and an input/output (IO) device 4 is connected to an information processing apparatus main body 10. The information processing apparatus main body 10 is formed of a general computer system including a processor and a memory for example. Components and functions, in the information processing apparatus main body 10, described below are each implemented by executing a computer program that can be stored in a computer-readable memory. This computer program is able to store a computer readable memory. The input device 2 may be a keyboard, a pointing device, or the like for example. The output device 3 may be a display device, a printer, or the like for example. The IO device 4 may be a large capacity storage device, a network interface device, or the like for example.

The information processing apparatus main body 10 includes a phantom image data storage unit 11, a digital phantom data storage unit 13, an H/M ratio data storage unit 15, a conversion function storage unit 17, a subject image data storage unit 19, a positioning processing unit 21, an ROI setting unit 23, an H/M ratio calculation unit 25, a conversion function calculation unit 27, and an H/M ratio conversion processing unit 29.

The phantom image data storage unit 11 stores pieces of phantom image data as pieces of data on phantom images obtained by capturing phantoms adjusted to be under a certain imaging condition in different imaging environments. The phantom image data is acquired through the input device 2 or the IO device 4 for example. For example, the phantom image data storage unit 11 stores the phantom image data for each imaging environment such as a first imaging environment and a second imaging environment and for each imaging condition. For example, the imaging environment is specified by a facility where the imaging device is installed, a model of the imaging device, a type of a collimator used for the imaging, and the like. The imaging condition is specified by a type of the phantom (difference of the configuration of the phantom described later), an imaging direction of the phantom (front or back in a plan view of the phantom having a flat plate shape described later), and the like.

In the present embodiment, the phantom image obtained by capturing an image of the phantom under a predetermined imaging condition is used. More specifically, the phantom images are images of phantom captured under a plurality of imaging conditions common among the imaging environments. For example, in the present embodiment, the phantom images captured under four different conditions in each imaging environment are used.

The common configuration of the phantom in the present embodiment will be described below. The phantom has a flat plate shape of a predetermined thickness resembling a cross-section of the chest of a human body. The phantom includes an inner space where liquid can be contained. The inner space of the phantom can contain a solution including medicine that is the same as that administered to the subject. The inner space of the phantom includes a human body (background) region and, in the human body region, regions respectively corresponding to organs such as a cardiac region, a thyroid region, a liver region, and a lung region that are fluidically communicated with each other. The configuration is described more in detail below with a specific example. The required organ region may differ in accordance with the type of the used medicine.

Figure 2:
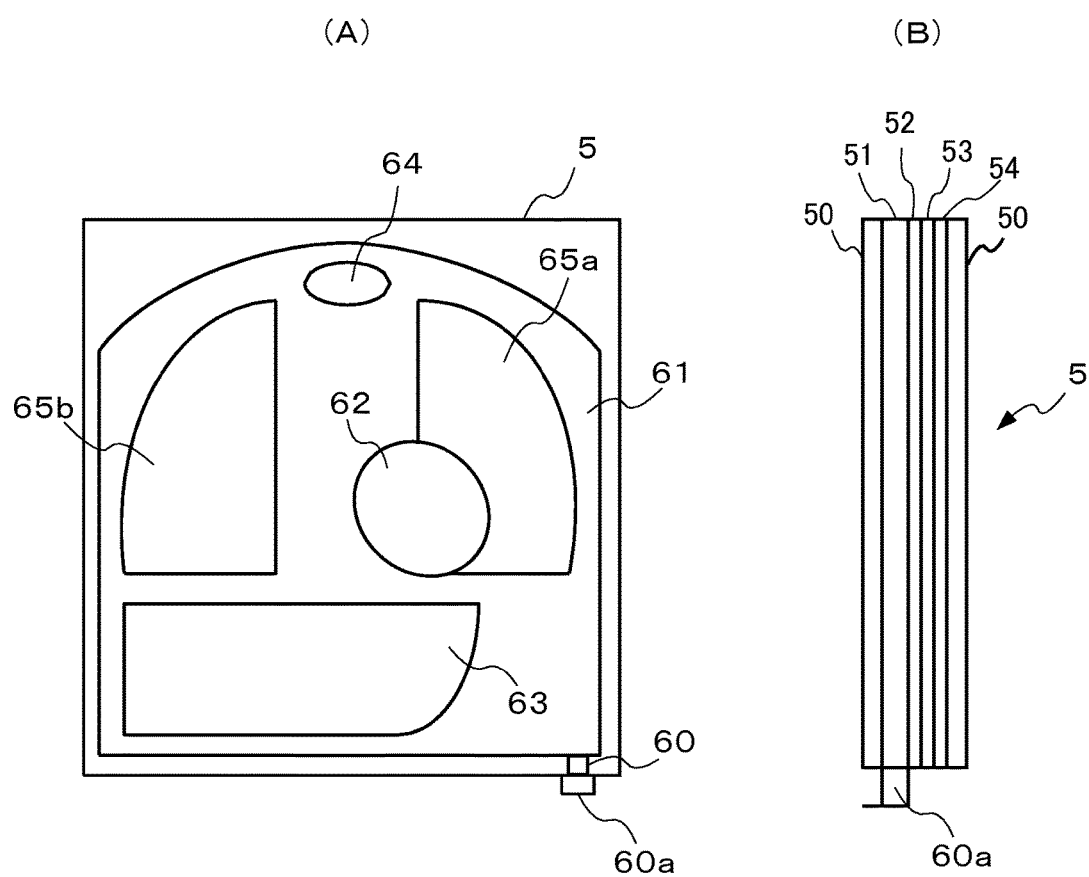
FIG. 2 illustrates an example of a phantom 5.

FIG. 2 illustrates an example of a phantom 5. FIG. 2A is a plan view of the phantom 5, and FIG. 2B is the side view of the phantom 5.

The phantom 5 illustrated in the figure has a four layer structure in which four transparent acrylic plates 51 to 54 are placed on top of the other in a stacked manner. The configuration of each of the acrylic plates 51 to 54 is described later. The four acrylic plates 51 to 54 are sandwiched by outer layer plates 50 that are transparent plate members made of the same material. The thickness of the outer layer plate 50 is 10 mm for example. In the plan view illustrated in FIG. 2A, the phantom 5 includes a human body region 61, a cardiac region 62, a liver region 63, a thyroid region 64, and lung regions 65 (65a and 65b). All of the regions 61 to 65 are in fluid communication with each other as described below. The communicated region is hereinafter referred to as the inner space. The phantom 5 further includes an injection/discharge port 60. The inner space of the phantom is in fluid communication with the outside through the injection/discharge port 60. Thus, liquid can be injected into and discharged from the inner space of the phantom 5 through the injection/discharge port 60. The injection/discharge port 60 is closed by a screw plug 60a, and thus the inner space is sealed.

Figure 3:
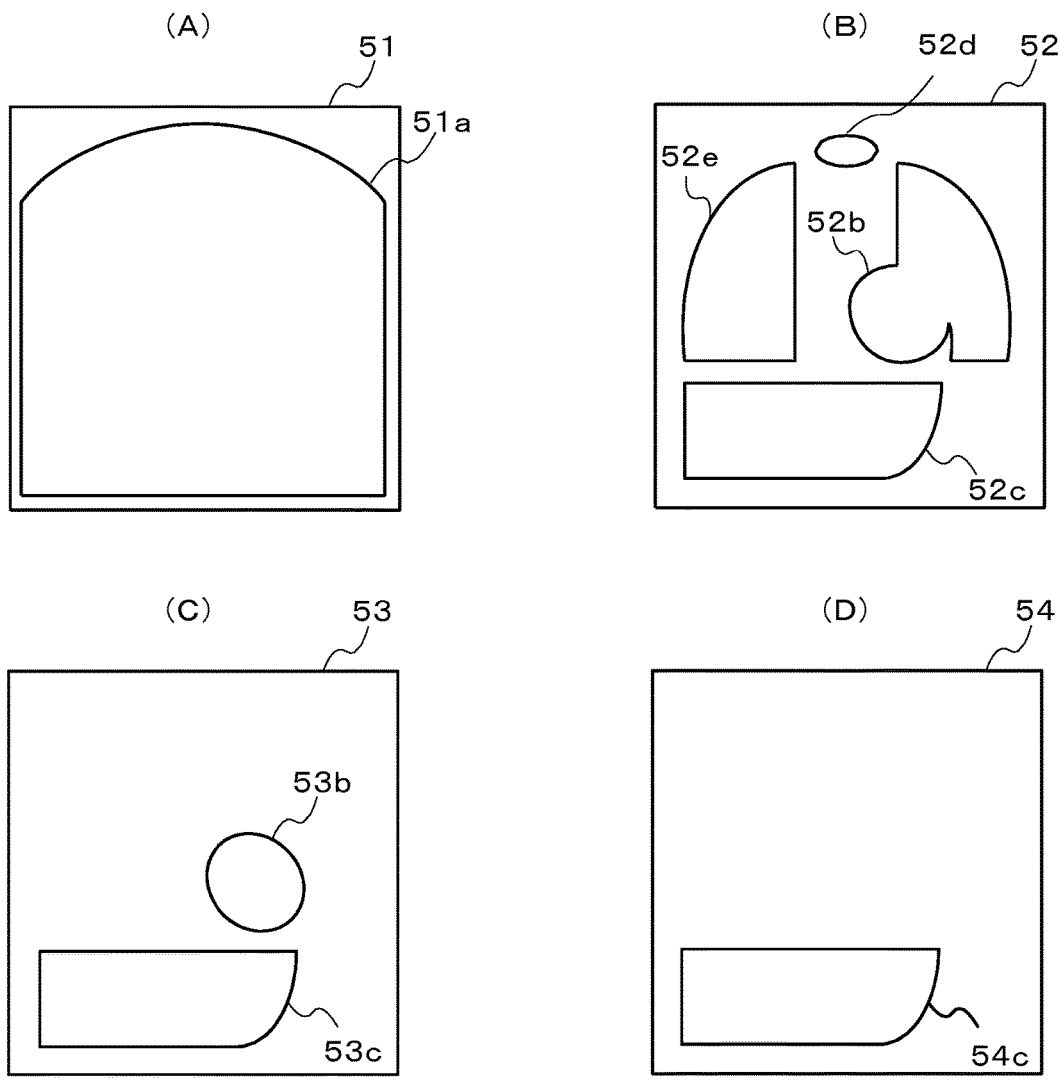
FIG. 3 is a plan view illustrating acrylic plates of four layers of the phantom 5.

FIG. 3 is a plan view illustrating the acrylic plates of four layers.

FIG. 3A illustrates the acrylic plate 51 as the first layer. The acrylic plate 51 includes an opening 51a for forming the human body region 61. The thickness of the acrylic plate 51 as the first layer is 15 mm for example.

FIG. 3B illustrates the acrylic plate 52 as the second layer. The acrylic plate 52 as the second layer includes openings 52b, 52c, 52d, and 52e for respectively forming the cardiac region 62, the liver region 63, the thyroid region 64, and the lung regions 65. The thickness of the acrylic plate 52 as the second layer is 5 mm for example.

FIG. 3C illustrates the acrylic plate 53 as the third layer. The acrylic plate 53 as the third layer includes openings 53b and 53c for respectively forming the cardiac region 62 and the liver region 63. The thickness of the acrylic plate 53 as the third layer is 5 mm for example.

FIG. 3D illustrates the acrylic plate 54 as the fourth layer. The acrylic plate 54 as the fourth layer includes an opening 54c for forming the liver region 63. The thickness of the acrylic plate 54 as the fourth layer is 5 mm for example.

When the acrylic plates 51 to 54 are stacked, the openings positioned at the same positions in the plan view are connected to each other in a thickness direction, whereby the inner space is formed. Due to the resultant differences among the human body region 61, the cardiac region 62, the liver region 63, the thyroid region 64, and the lung regions 65 in the length in the thickness direction, the solutions respectively in the regions 61 to 65 are different from each other in the depth in the thickness direction. For example, the cardiac region 62 is formed of the openings 51a, 52b, and 53b, and the thyroid region 64 is formed of the openings 51a and 52d. As a result, when the inner space is filled with the solution at a uniform drug concentration, the regions 61 to 65 are different from each other in the accumulated radioactivity amount per unit area corresponding to the thicknesses.

The thicknesses of the acrylic plates 51 to 54 as the first to the fourth layers and the outer layer plates 50 are not limited to those described above. Thus, the phantom may include the acrylic plates 51 to 54 as the first to the fourth layers and the outer layer plates 50 having the thicknesses different from the above described thicknesses. In the present embodiment, phantom images captured by using a plurality of types of phantoms different from each other in the thicknesses of the first to the fourth layers are used. Thus, the phantom image data storage unit 11 stores data of at least four phantom images under different imaging conditions, obtained by capturing an image of the two types of phantoms from front and back in each imaging environment.

Referring back to FIG. 1, the digital phantom data storage unit 13 stores digital phantom data. For example, the digital phantom data is acquired through the input device 2 or the IO device 4. The digital phantom data is data indicating a shape of the actual phantom 5 described above in the plan view. Thus, the digital phantom data indicates the relative positions and the shapes of the regions 61 to 65 in the phantom 5 illustrated in FIG. 2A. The digital phantom data further includes data for setting a region of interest (ROI) in a predetermined region. For example, the digital phantom data in the present embodiment includes data indicating regions for setting a cardiac ROI and a mediastinum ROI.

The H/M ratio data storage unit 15 stores data on the H/M ratio calculated by the H/M ratio calculation unit 25. The H/M ratio data storage unit 15 may also store data on the H/M ratio acquired from the input device 2 or the IO device 4.

The conversion function storage unit 17 stores data indicating a conversion function calculated by the conversion function calculation unit 27. For example, the conversion function storage unit 17 stores the conversion function and the identification information of the imaging environment before and after the conversion that are associated with each other. The identification information of the imaging environment may be a combination of a facility name, a model of the imaging device, a type of the collimator, and the like. The conversion function for converting a certain imaging environment to a theoretical H/M ratio described later is associated with information indicating the conversion from the imaging environment before the conversion into a theoretical value. The conversion function storage unit 17 may store data on the conversion function acquired from the input device 2 or the IO device 4.

The subject image data storage unit 19 stores image data of a subject image as a planer image obtained by capturing an image of the subject administered with the MIBG. For example, the subject image data is acquired through the input device 2 or the IO device 4. Each pixel value of the subject image represents a count value in the RI. Each subject image is associated with information indicating the imaging environment.

The positioning processing unit 21 acquires the phantom image data stored in the phantom image data storage unit 11 and the digital phantom data stored in the digital phantom data storage unit 13, and performs positioning processing to position the digital phantom data on the phantom image. For example, the positioning processing may be executed by using a known positioning algorithm. The digital phantom data includes the cardiac ROI and the mediastinum ROI respectively corresponding to the cardiac region and a mediastinum region in the phantom image. Thus, when the digital phantom is positioned on the phantom image data, the cardiac ROI and the mediastinum ROI are automatically set. All things considered, the positioning processing unit 21 sets the ROIs through positioning of the digital phantom.

Thus, the standardized ROI setting to the phantom image is achieved. Thus, a higher accuracy of the H/M ratio can be achieved with no difference between practitioners in the ROI setting.

The positioning processing unit 21 may similarly perform positioning of the digital phantom on the subject image stored in the subject image data storage unit 19.

The ROI setting unit 23 acquires subject image data from the subject image data storage unit 19 and sets the ROI in a predetermined region in the subject image. For example, the ROI setting unit 23 sets the cardiac ROI and the mediastinum ROI respectively to the cardiac region and the mediastinum region in the subject image. For example, a method described in PTL 1 may be used in the ROI setting. The processing executed by the ROI setting unit 23 may be omitted when an operator manually sets the ROIs.

When the digital phantom is positioned on the subject image by the positioning processing unit 21, the ROI setting by the ROI setting unit 23 may be omitted.

The H/M ratio calculation unit 25 calculates the H/M ratio based on the phantom image data or the subject image data. For example, the H/M ratio calculation unit 25 calculates the H/M ratio based on the pixel values (count values) in the cardiac ROI and the mediastinum ROI set to the phantom image or the subject image. For example, the H/M ratio calculation unit 25 calculates an average value of the count values in the cardiac ROI and an average value of the count values in the mediastinum ROI, and then calculates the ratio between the average values with the average value of the count values in the mediastinum ROI being a denominator. The H/M ratio calculation unit 25 calculates the H/M ratio based on a target image, regardless of whether the target image is the phantom image or the subject image. The output device 3 may display the H/M ratio calculated by the H/M ratio calculation unit 25.

The conversion function calculation unit 27 calculates a conversion function for converting the H/M ratio obtained from a certain imaging environment into an H/M ratio obtained from another imaging environment or the theoretical H/M ratio. Data on the conversion function thus calculated is stored in the conversion function storage unit 17.

Figure 4:
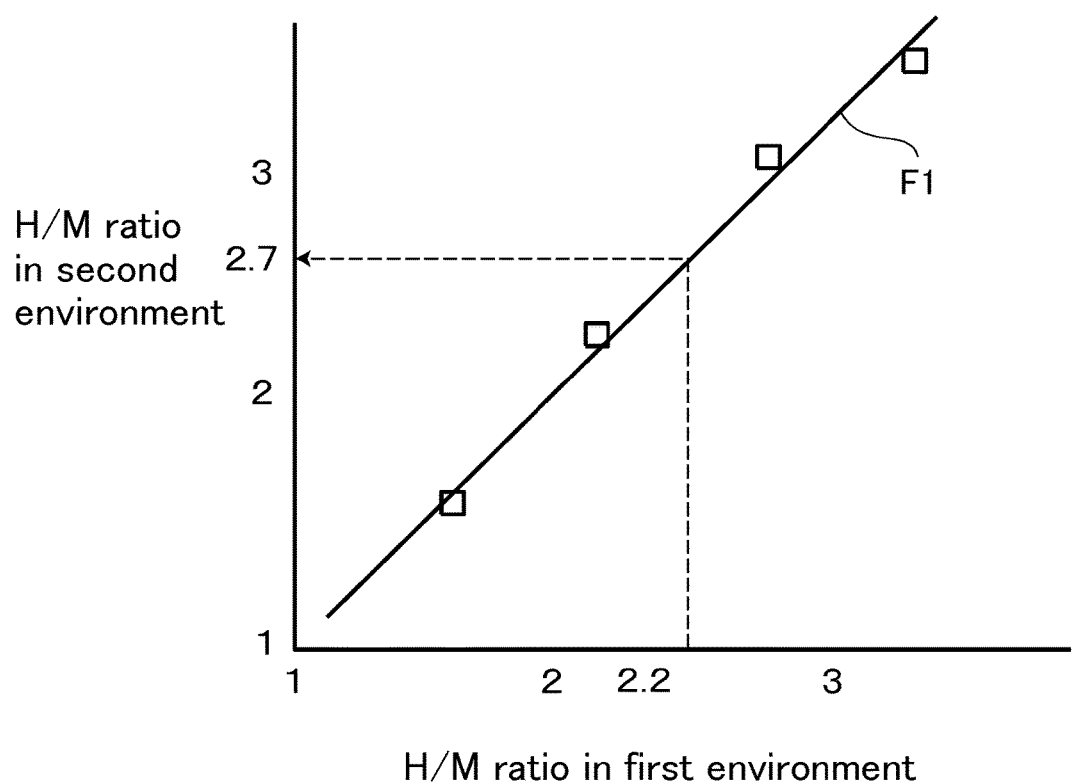
FIG. 4 illustrates a conversion function.

For example, as illustrated in FIG. 4, the conversion function calculation unit 27 calculates a conversion function F1 for converting an H/M ratio calculated from an image captured in a certain imaging environment (first imaging environment) into an H/M ratio to be calculated from an image captured in another imaging environment (second imaging environment). The conversion function calculation unit 27 reads out from the H/M ratio data storage unit 15, data on a plurality of H/M ratios calculated from the phantom images captured under a plurality of imaging conditions in the first imaging environment, and on a plurality of the H/M ratios calculated from the phantom images captured under the same imaging conditions in the second imaging environment. Then, the conversion function calculation unit 27 plots the H/M ratios on a graph illustrated in FIG. 4 with the H/M ratios under the same imaging conditions associated with each other, and performs a regression analysis to obtain a function for converting one of the H/M ratios into the other.

With the conversion function, for example, H/M ratios respectively calculated from images captured in different facilities such as a facility including the first imaging environment and a facility including the second imaging environment can be compared with each other. Furthermore, with the conversion function calculation unit 27, a conversion function can be calculated with which an H/M ratio, calculated from an image captured in the imaging environment before a change of the imaging environment such as replacing of the imaging device, and an H/M ratio, calculated from the image captured by the changed imaging device in the same facility, can be compared with each other.

The conversion function calculation unit 27 calculates a function for standardizing the H/M ratio calculated from an image captured in a certain imaging environment into a theoretical value independent from any imaging environments. The conversion function calculation unit 27 reads out from the H/M ratio data storage unit 15, H/M ratios calculated from phantom images captured under a plurality of imaging conditions in a certain imaging environment. As the imaging conditions, the configuration (for example, a material, a thickness, and the like) of the phantom, the type, the concentration, and the like of the medicine accommodated in the inner space are adjusted to be in predetermined states. The H/M ratio, obtained from a phantom image, is theoretically determined based on the imaging conditions and while taking scattering and absorption of radiation by the phantom into consideration. Thus, the conversion function calculation unit 27 performs the regression analysis based on the H/M ratio obtained from the captured phantom image and the theoretical H/M ratio to obtain a conversion function for converting one of the H/M ratios into the other.

As described above, the ROIs are automatically set to the phantom image by using the digital phantom, whereby a higher accuracy of the H/M ratio can be achieved. In the present embodiment, the conversion function is calculated by using the H/M ratio and thus can also be calculated accurately.

The H/M ratio conversion processing unit 29 acquires data on a desired conversion function from the conversion function storage unit 17, and converts the H/M ratio stored in the H/M ratio data storage unit 15. For example, the H/M ratio conversion processing unit 29 converts the H/M ratio calculated from the subject image captured in the first imaging environment into the H/M ratio to be calculated from the subject image captured in the second imaging environment as follows. Specifically, the H/M ratio conversion processing unit 29 acquires data of a conversion function corresponding to this conversion from the conversion function storage unit 17, and uses the conversion function to execute conversion processing on the H/M ratio stored in the H/M ratio data storage unit 15. Alternatively, the H/M ratio conversion processing unit 29 converts the H/M ratio calculated from the subject image captured in a certain imaging environment into the theoretical H/M ratio in a similar manner.

As described above, the conversion function is highly accurate, and thus the H/M ratio obtained from the subject image can be converted with a high accuracy.

The information processing apparatus according to the present embodiment having the configuration described above calculates the conversion function and executes the conversion processing on the H/M ratio through procedures described below.

Figure 5:
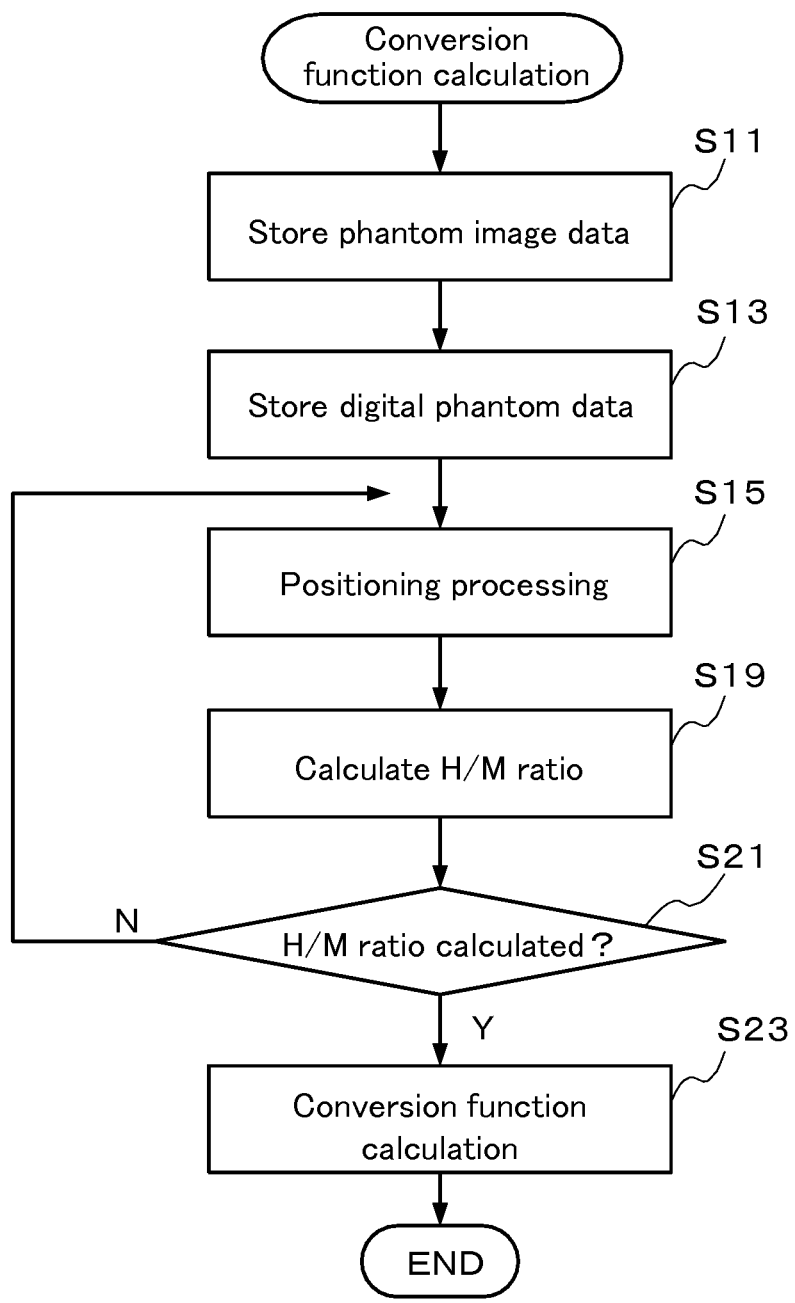
FIG. 5 is a flowchart illustrating a procedure of calculating the conversion function.

FIG. 5 is a flowchart illustrating the procedure for calculating the conversion function. Here, the processing calculating a function for converting the H/M ratio obtained from the first imaging environment into the H/M ratio obtained from the second imaging environment and a function for converting the H/M ratio obtained from the first imaging environment into the theoretical H/M ratio are described.

In the first and the second imaging environments, pieces of image data of a plurality of phantom images captured under a predetermined imaging condition are stored in the phantom image data storage unit 11 (S11). The image data is stored while being associated with identification information indicating the imaging environment and the imaging condition used for capturing the corresponding one of the phantom images. The digital phantom data is stored in the digital phantom data storage unit 13 (S13). For example, the image data and the digital phantom data may be acquired from the outside through the IO device 4. The processing thereafter can only be executed after the phantom image data and the digital phantom data are prepared. Either one of steps S11 and S13 may be executed first. Furthermore, any one of steps S11 and S13 may be omitted if the corresponding data has been prepared. In the present embodiment, the processing at and after step S15 is executed after the pieces of data on a plurality of phantom images are stored in the phantom image data storage unit 11. Alternatively, the processing at and after step S15 may be executed every time the image data on a single phantom image is stored in the phantom image data storage unit 11.

The positioning processing unit 21 reads out image data on a single phantom image as the processing target from the phantom image data storage unit 11. The positioning processing unit 21 further reads out the digital phantom data from the digital phantom data storage unit 13. The positioning processing unit 21 performs positioning of the digital phantom on the phantom image that is the processing target. Thus, at the same time, the ROIs are set to the cardiac region and the mediastinum region in the phantom image (S15).

The H/M ratio calculation unit 25 calculates the H/M ratio based on the count values in the images in the ROIs set to the phantom image in step S15 (S19). The data on the H/M ratio thus calculated is stored in the H/M ratio data storage unit 15.

Then, the processing returns to step S15 (S21: No), whereby the H/M ratio calculation processing is repeated until the H/M ratio is calculated for all the phantom images that are the processing targets.

When the H/M ratio is calculated for all the phantom images that are the processing targets (S21: Yes), the conversion function calculation unit 27 reads out the pieces of data on the H/M ratios calculated from the phantom images captured from the first and the second imaging environments from the H/M ratio data storage unit 15, and calculates the conversion function between the two environments (S23). The conversion function for converting the H/M ratio obtained from the first imaging environment into the theoretical H/M ratio is calculated by using the theoretical H/M ratio obtained from each imaging condition stored in the conversion function calculation unit 27 in advance. The data indicating the conversion function calculated by the conversion function calculation unit 27 is stored in the conversion function storage unit 17.

The information related to the conversion function thus calculated may be output by the output device 3.

Figure 6:
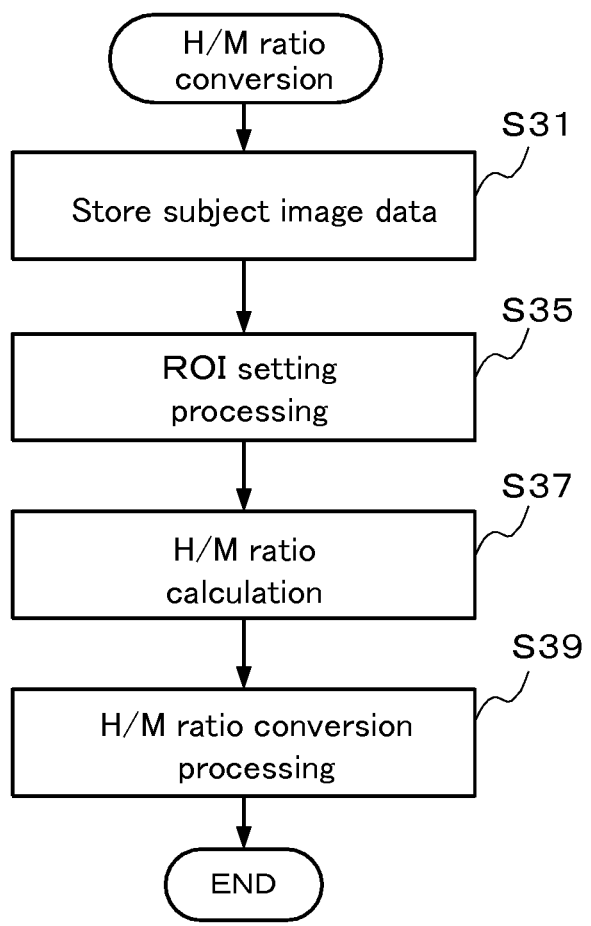
FIG. 6 is a flowchart illustrating a procedure of converting an H/M ratio.

FIG. 6 is a flowchart illustrating a procedure for converting the H/M ratio, obtained from an image of the subject captured in the first imaging environment, by using the conversion function described above.

Image data on a subject image obtained by capturing the subject administered with the MIBG in the first imaging environment is stored in the subject image data storage unit 19 (S31). For example, the image data may be acquired from the outside through the IO device 4. The processing thereafter can be only executed after the subject image data is prepared. When the subject image data has already been prepared, step S31 may be omitted.

The ROI setting unit 23 reads out the image data on the subject image as the processing target from the subject image data storage unit 19. The ROI setting unit 23 further sets the ROIs to the cardiac region and the mediastinum region in the subject image as the processing target (S35).

The H/M ratio calculation unit 25 calculates the H/M ratio based on the count values in the images in the ROIs set in step S35 (S37). The data on the H/M ratio thus calculated is stored in the H/M ratio data storage unit 15.

The H/M ratio conversion processing unit 29 reads out the data on the H/M ratio calculated in step S37 from the H/M ratio data storage unit 15, and reads out the data on a desired conversion function from the conversion function storage unit 17. Then, the H/M ratio conversion processing unit 29 converts the H/M ratio by using the conversion function (S39). For example, the H/M ratio conversion processing unit 29 reads out the data on the conversion function for converting the first imaging environment into the second imaging environment from the conversion function storage unit 17, and converts the H/M ratio obtained from the first imaging environment into the H/M ratio obtained from the second imaging environment. Alternatively, the H/M ratio conversion processing unit 29 reads out the data on the conversion function for converting the H/M ratio obtained from the first imaging environment into the theoretical H/M ratio from the conversion function storage unit 17, and converts the H/M ratio obtained from the first imaging environment into the theoretical value.

The H/M ratios before and after the conversion may be output by the output device 3.

With the present embodiment, the H/M ratios respectively calculated from images of the subject, administered with a diagnostic medicine such as MIBG, captured in different imaging environments can be accurately compared with each other. In particular, by converting the H/M ratio into the theoretical value, the H/M ratio can be accurately standardized into an H/M ratio independent from the imaging environment.

An information processing apparatus according to a second embodiment of the present invention is described below with reference to the drawings. The components that are the same as those in the first embodiment are denoted with the same reference numerals and the description thereof will be omitted.

The information processing apparatus according to the present embodiment executes processing of obtaining a function for calculating an index indicating a probability of the occurrence of a predetermined event. For example, the predetermined event in the present embodiment is living or dying of a patient with heart failure after a predetermined period (for example, after 5 years). The index indicates whether the predetermined event occurs in the future, and is an index (5 year mortality risk) indicating the probability of the patient being alive after 5 years in the present embodiment.

Figure 7:
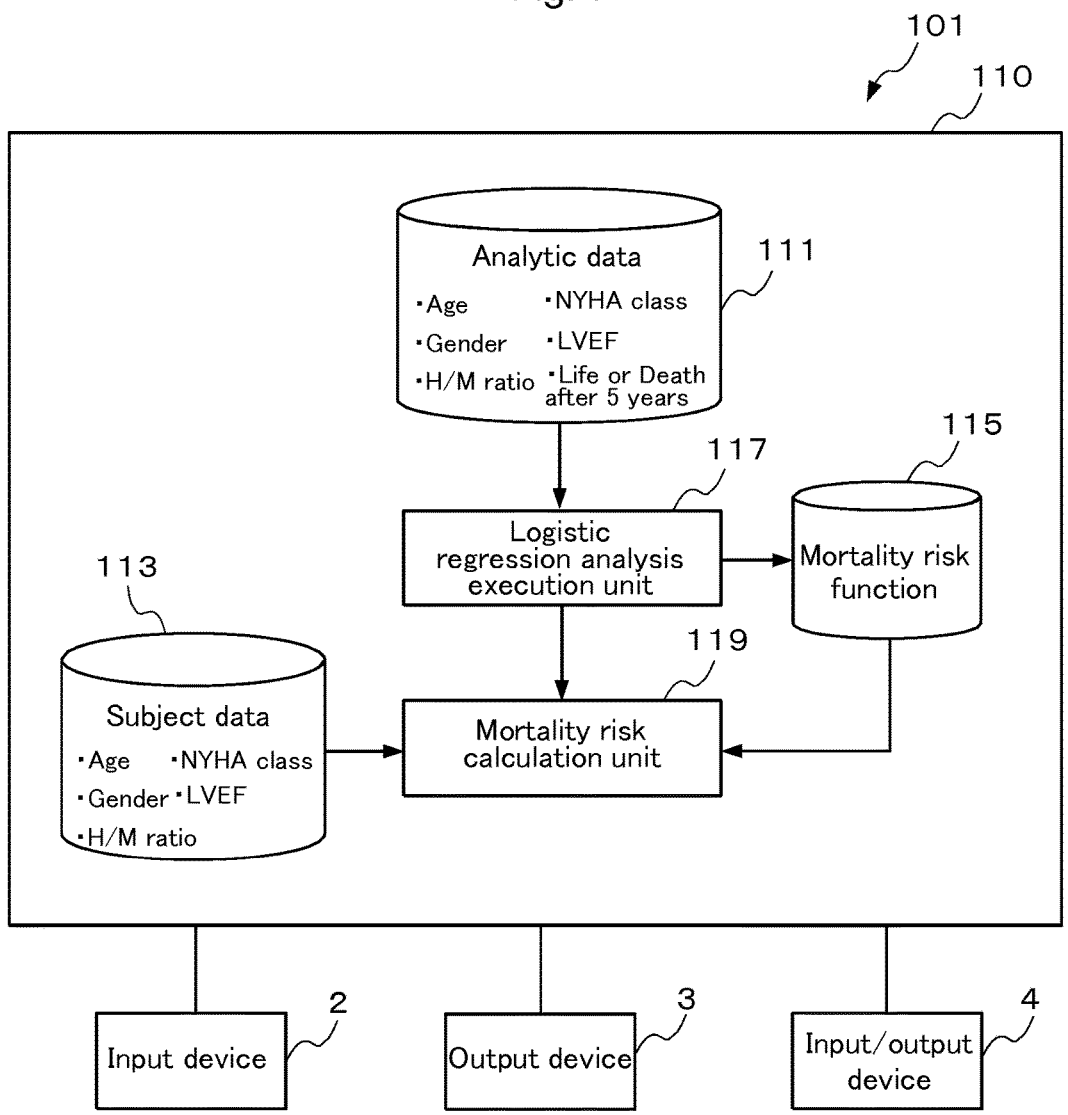
FIG. 7 illustrates an overall configuration of an information processing apparatus 101 according to another embodiment of the present invention.

FIG. 7 illustrates an overall configuration of an information processing apparatus 101 according to the present embodiment. As illustrated in the figure, in the information processing apparatus 101, at least one of the input device 2, the output device 3, and the IO device 4 is connected to an information processing apparatus main body 110. The information processing apparatus main body 110 is formed of a general computer system including a processor and a memory for example. Components and functions, in the information processing apparatus main body 110, described below are each implemented by executing a computer program. The computer program can be stored in a computer-readable memory.

The information processing apparatus main body 110 includes an analytical data storage unit 111, a subject data storage unit 113, a mortality risk function storage unit 115, a logistic regression analysis execution unit 117, and a mortality risk calculation unit 119.

The analytical data storage unit 111 stores analytical data related to regular or irregular test performed on a large number of subjects (corresponding to a second subject) with heart failure in one or a plurality of facilities. The analytical data includes the age, the gender, a heart/mediastinum ratio (H/M ratio), an index (for example, New York Heart Association (NYHA) class) indicating the severity of the heart failure, an index (for example, Left Ventricular Ejection Fraction (LVEF)) indicating a left ventricular function, and life or death after 5 years. For example, the analytical data is acquired through the input device 2 or the TO device 4. The age, the gender, the H/M ratio, the index indicating the severity of the heart failure, and the index indicating the left ventricular function correspond to subject data on the second subject, and life or death after 5 years corresponds to event data.

The age is the age of each subject at the time of the test. The gender is the gender of each subject and is male or female.

The H/M ratio may be a heart/mediastinum ratio acquired from an RI planer image obtained by detecting radioactivity from the subject that has been administered with MIBG ($^{123}$I-3-iodobenzylguanidine) as a diagnostic medicine, as described in the first embodiment. The H/M ratio stored in the analytical data storage unit 111 may be data on the H/M ratio calculated by the H/M ratio calculation unit 25 in the first embodiment, and may be a standardized H/M ratio independent from the imaging environment obtained by the conversion by the H/M ratio conversion processing unit 29. The H/M ratio stored in the analytical data storage unit 111 may also be an H/M ratio obtained from the second imaging environment obtained by the conversion by the H/M ratio conversion processing unit 29.

The NYHA class indicates classes of severity of the heart failure determined by the New York Heart Association. More specifically, the severity of the heart failure is classified into four classes by comprehensively evaluating images, medical interviews, and the like:

NYHA class I: a cardiac disease patient, but no symptoms and no limitation in ordinary activity.

NYHA class II: a cardiac disease patient with slight or intermediate limitation during ordinary activity. No symptoms at rest. Fatigue, palpitation, breathing difficulty and/or angina during ordinary activity.

NYHA class III: a cardiac disease patient with marked limitation on ordinary activity. No symptoms at rest. Symptoms during less-than-ordinary activity, e.g. walking on flat land.

NYHA class IV: a cardiac disease patient that experiences symptoms even during extremely mild activity, and may experience symptoms such as heart failure or angina even during rest.

The LVEF is a left ventricular ejection rate and an index indicating contractile force of the left ventricle. For example, the LVEF is acquired by an analysis on an ultrasonic echo image, and indicates the percentage of the capacity of the left ventricle ejected by a single ejection.

The life or death after 5 years is data indicating whether the subject that has went through the cardiac function test is alive (alive or dead) 5 years after the test. Thus, the data on the life or death after 5 years is historic data indicating whether the predetermined event has occurred.

The subject data storage unit 113 stores subject data on a subject (corresponding to a first subject), as a calculation target of the 5 year mortality risk described below. The subject data includes the age, the gender, the H/M ratio, the NYHA class, and the LVEF of the subject for example. The subject data may be the subject data on a single subject or may be subject data on a plurality of subjects. For example, the subject data is acquired through the input device 2 or the IO device 4.

The H/M ratio stored in the subject data storage unit 113 may be data on the H/M ratio calculated by the H/M ratio calculation unit 25 in the first embodiment, and may be a standardized H/M ratio independent from the imaging environment obtained by the conversion by the H/M ratio conversion processing unit 29. The H/M ratio stored in the subject data storage unit 113 may also be an H/M ratio obtained from the second imaging environment obtained by the conversion by the H/M ratio conversion processing unit 29. Any of the H/M ratios described above may be stored in the subject data storage unit 113 and the analytical data storage unit 111. Still, when the standardized H/M ratio independent from the imaging environment or the H/M ratio obtained from the second imaging environment is stored in both of the storage units and is used for obtaining the 5 year mortality risk function described later and for calculating the 5 year mortality risk, a more accurate function for the 5 year mortality risk can be obtained and more accurate 5 year mortality risk can be calculated.

The mortality risk function storage unit 115 stores the 5 year mortality risk function calculated by the logistic regression analysis execution unit 117.

The logistic regression analysis execution unit 117 reads out the analytical data stored in the analytical data storage unit 111, and executes a known logistic regression analysis to obtain a function related to the 5 year mortality risk (5 year mortality risk=F (the age, the gender, the H/M ratio, the NYHA class, and the LVEF)). Thus, the function related to the 5 year mortality risk is determined in accordance with the history of an occurrence (life or death after 5 years) of the predetermined event, and is used for calculating an index indicating the probability of the occurrence of the event in the future. The age, the gender, the H/M ratio, the NYHA class, and the LVEF in the analytical data are independent variables (explanatory variables) in the logistic regression analysis, and the 5 year mortality risk in the analytical data is the dependent variable (objective variable) in the logistic regression analysis.

The mortality risk calculation unit 119 reads out the subject data stored in the subject data storage unit 113 and the 5 year mortality risk function stored in the mortality risk function storage unit 115 to calculate the 5 year mortality risk. More specifically, the 5 year mortality risk is calculated by substituting the age, the gender, the H/M ratio, the NYHA class, and the LVEF in the subject data into the 5 year mortality risk function. The 5 year mortality risk may be represented with percentages or may be represented as alive or dead. The 5 year mortality risk thus calculated may be displayed on the output device 3, or may be printed and output by the output device 3. Alternatively, the 5 year mortality risk thus calculated may be stored in an unillustrated storage unit.

The information processing apparatus 101 according to the present embodiment having the configuration described above obtains the 5 year mortality risk function and calculates the 5 year mortality risk through the procedure described below (calculates an index indicating a probability of an occurrence of the predetermined event).

Figure 8:
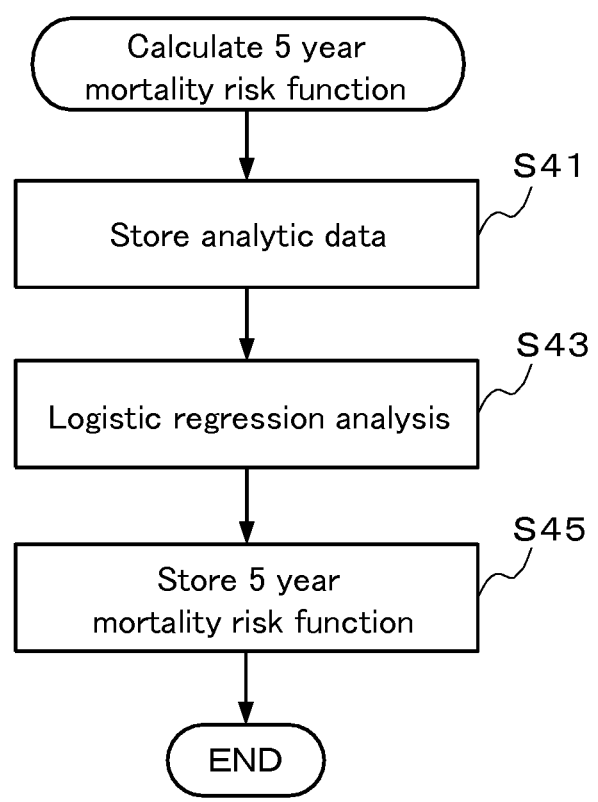
FIG. 8 is a flowchart illustrating a procedure of obtaining a five year mortality risk function.

FIG. 8 is a flowchart illustrating a procedure of obtaining the 5 year mortality risk function. First of all, the analytical data related to the tests performed on a large number of subjects with heart failure is stored in the analytical data storage unit 111 (S41). The analytical data may be acquired from the outside through the IO device 4. This step may be omitted when the analytical data has already been prepared.

Next, the logistic regression analysis execution unit 117 reads out the analytical data stored in the analytical data storage unit 111, executes the logistic regression analysis, and obtains the function related to the 5 year mortality risk (5 year mortality risk=F (the age, the gender, the H/M ratio, the NYHA class, and the LVEF)) (S43). The function related to the 5 year mortality risk thus obtained is stored in the mortality risk function storage unit 115 (S45).

Figure 9:
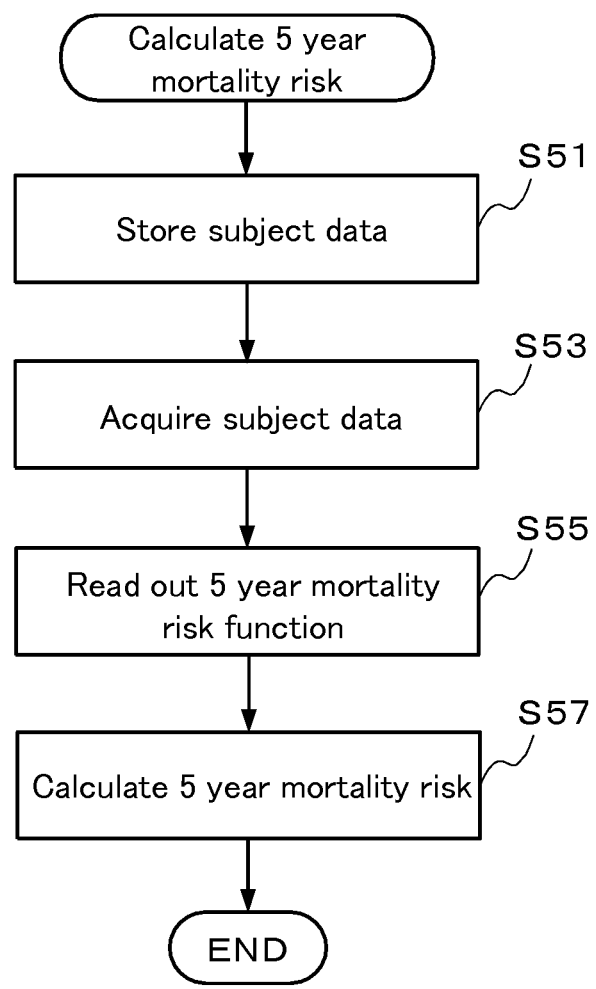
FIG. 9 is a flowchart illustrating a procedure of calculating a five year mortality risk.

FIG. 9 is a flowchart illustrating a procedure of calculating the 5 year mortality risk. First of all, the subject data is stored in the subject data storage unit 113 (S51). The subject data may be acquired from the outside through the IO device 4. This step may be omitted when the subject data has already been prepared.

Then, the mortality risk calculation unit 119 acquires the subject data stored in the subject data storage unit 113 (S53), and reads out the 5 year mortality risk function stored in the mortality risk function storage unit 115 (S55). Then, the 5 year mortality risk is calculated by substituting the subject data (the age, the gender, the H/M ratio, the NYHA class, and the LVEF) into the 5 year mortality risk function thus read out (S57). The 5 year mortality risk thus calculated may be displayed on the output device 3 or may be printed and output by the output device 3.

In the present embodiment, the logistic regression analysis is performed with the age, the gender, the H/M ratio, the NYHA class, and the LVEF selected as the independent variables from a large number of variables as candidates of the independent variables. Thus, a highly accurate function related to the 5 year mortality risk can be obtained. Thus, a highly accurate 5 year mortality risk can be calculated. By using a standardized H/M ratio independent from the imaging environment or the H/M ratio obtained from the second imaging environment, an even more accurate function related to the 5 year mortality risk can be obtained, and thus an even more accurate 5 year mortality risk cab be calculated.

Embodiments of the present inventions are examples for describing the present invention. The scope of the present invention is not limited to the embodiments. Thus, the person skilled in the art can implement the present invention in various other forms without departing from the gist of the present invention.

For example, in the first embodiment described above, the H/M ratio is calculated based on the phantom image data and the digital phantom data, and the conversion function is calculated based on the H/M ratio thus calculated. Alternatively, the H/M ratios calculated in advance from the phantom image captured in and under various imaging environments and imaging conditions may be stored in the H/M ratio data storage unit 15, and the conversion function may be calculated by the conversion function calculation unit 27 based on the H/M ratio stored in the H/M ratio data storage unit 15. The H/M ratios calculated from the phantom image captured in and under various imaging environments and imaging conditions may be stored in the H/M ratio data storage unit 15 through the TO device 4.

Figure 10:
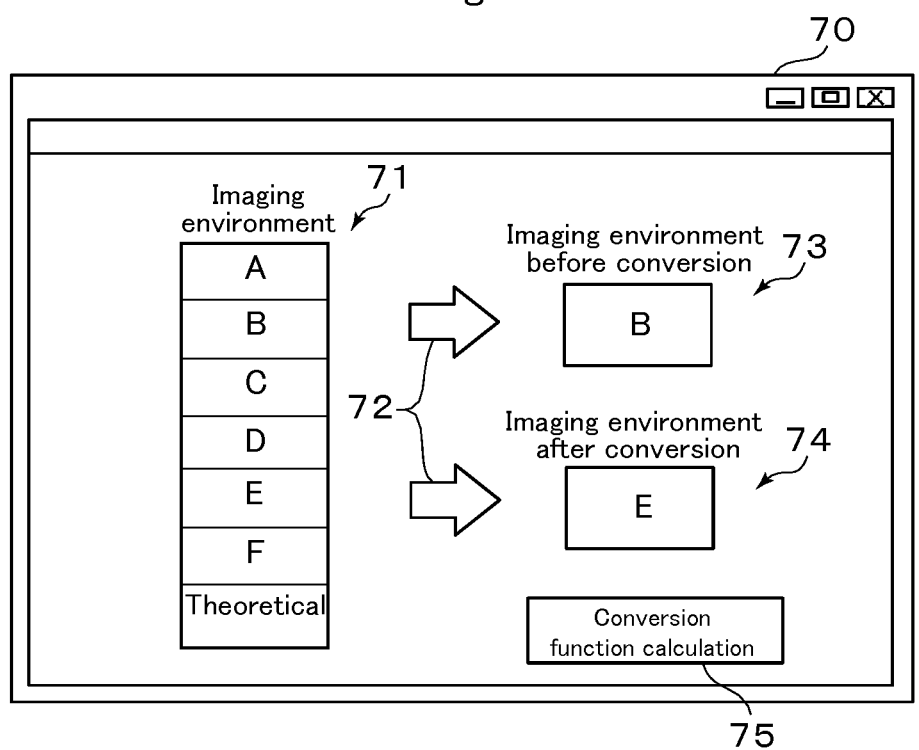
FIG. 10 illustrates an imaging environment selection window 70 for selecting an imaging environment.

FIG. 10 illustrates an imaging environment selection window 70 that is displayed on a display of the output device 3 and is used for selecting the imaging environment.

As illustrated in FIG. 10, the imaging environment selection window 70 displays a list 71 of imaging environments corresponding to the H/M ratios stored in the H/M ratio data storage unit 15. The list 71 further displays "theoretical" for calculating the function for converting the H/M ratio obtained from the first imaging environment into the theoretical H/M ratio and the function of converting the theoretical H/M ratio into the H/M ratio obtained from the first imaging environment. When the user selects the imaging environment from the list 71 and clicks an arrow 72, the selected imaging environment is displayed on a before conversion imaging environment display field 73 and an after conversion imaging environment display field 74. When a conversion function calculation button 75 is clicked, the conversion function is calculated as follows.

Figure 11:
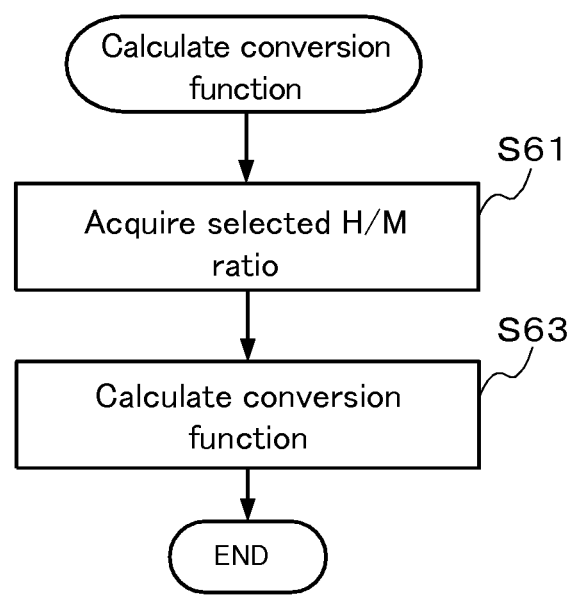
FIG. 11 is a flowchart illustrating a procedure of calculating a conversion function.

FIG. 11 is a flowchart illustrating a procedure of calculating the conversion function executed by the conversion function calculation unit 27. The processing described herein is for calculating the function for converting the H/M ratio obtained from the first imaging environment into the H/M ratio obtained from the second imaging environment, the function for converting the H/M ratio obtained from the first imaging environment into the theoretical H/M ratio, and the function for converting the theoretical H/M ratio into the H/M ratio obtained from the first imaging environment.

The conversion function calculation unit 27 acquires, from the H/M ratio data storage unit 15, the pieces of data on the H/M ratios corresponding to the first and the second imaging environments that have been selected (S61). Then, the conversion function calculation unit 27 calculates the conversion function between the two environments based on the acquired pieces of data (S63). When the conversion function for converting the H/M ratio obtained from the first imaging environment into the theoretical H/M ratio or the conversion function for converting the theoretical H/M ratio into the H/M ratio obtained from the first imaging environment is calculated by using the theoretical H/M ratio for each image condition stored in the conversion function calculation unit 27 in advance. For example, when the conversion function for converting the H/M ratio obtained from the first imaging environment into the theoretical H/M ratio is calculated, an inverse function can be obtained therefrom as the conversion function for converting the theoretical H/M ratio into the H/M ratio obtained from the first imaging environment. Thus, the conversion function calculation unit 27 may calculate the conversion function in one direction and at the same time calculate the inverse function therefrom as the conversion function in the opposite direction. The data indicating the conversion function calculated by the conversion function calculation unit 27 is stored in the conversion function storage unit 17.

Figure 12:
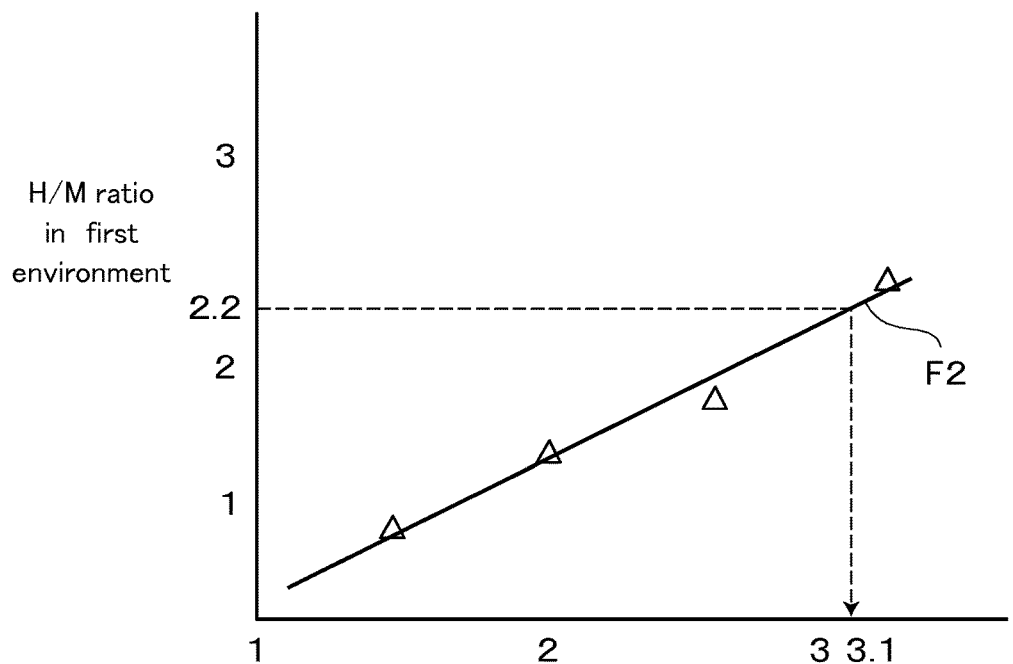
FIG. 12 illustrates a first conversion function and a second conversion function.
Figure 12:
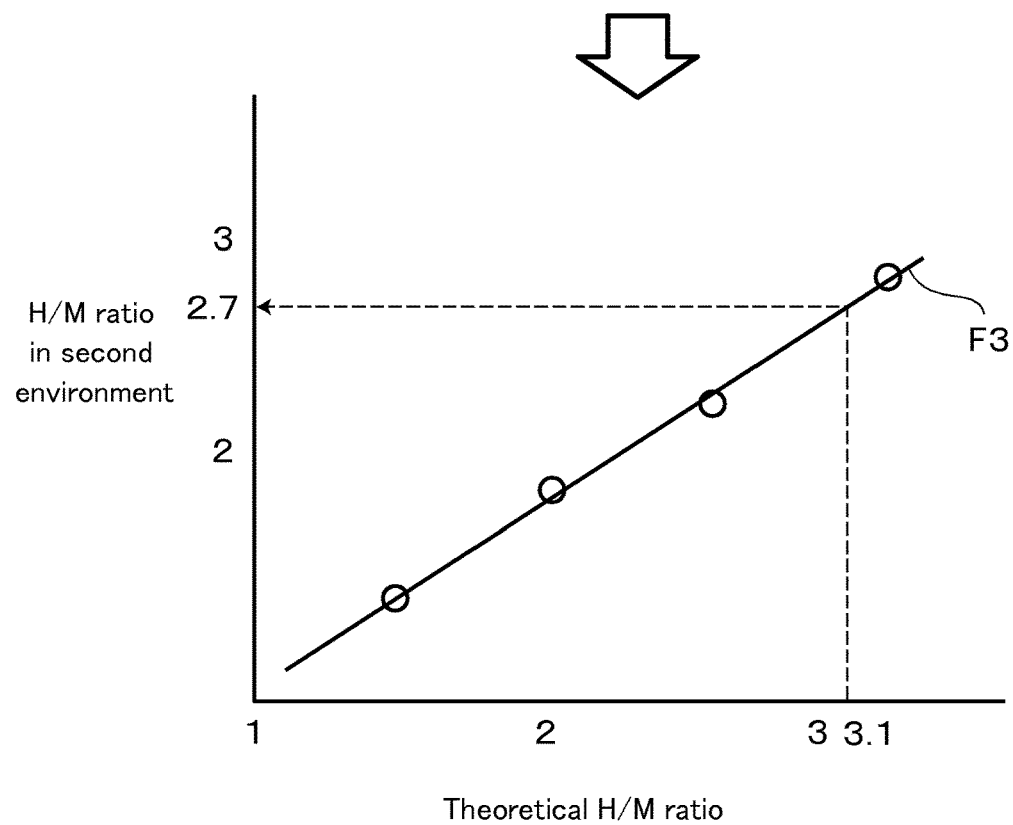

When the function for converting the H/M ratio obtained from the first imaging environment into the H/M ratio obtained from the second imaging environment is calculated, the conversion function F1 illustrated in FIG. 4 for directly converting the H/M ratio obtained from the first imaging environment into the H/M ratio obtained from the second imaging environment may be calculated. Alternatively, a first conversion function F2 for converting the H/M ratio obtained from the first imaging environment into the theoretical H/M ratio and a second conversion function F3 for converting the theoretical H/M ratio into the H/M ratio obtained from the second imaging environment as illustrated in FIG. 12 may be calculated. By thus calculating the conversion function for converting between H/M ratios obtained from a predetermined imaging environment and the theoretical H/M ratio, an H/M ratio obtained from a desired imaging environment can be acquired by appropriately combining two of a plurality of conversion functions. When an H/M ratio obtained from a third imaging environment is to be converted into the H/M ratio obtained from the second imaging environment, a conversion function for the direct conversion does not necessarily have to be calculated. Instead, a conversion function for converting the H/M ratio obtained from the third imaging environment into the theoretical H/M ratio may be calculated in advance and may be combined with the conversion function F3, whereby the H/M ratio obtained from the third imaging environment can be converted into the H/M ratio obtained from the second imaging environment. Thus, the conversion functions can be more simply associated with each other and can be managed more easily.

The H/M ratio stored in the H/M ratio data storage unit 15 is used as the H/M ratio of the phantom. Alternatively, H/M ratios corresponding to a plurality of imaging environments stored in a server connected through a network may be recognized. Thus, the imaging environments may be displayed on the list 71 in the imaging environment selection window 70, and the H/M ratio obtained from the selected imaging environment may be acquired from the server.

In the embodiments described above, the conversion function calculation unit 27 calculates the conversion function, and the H/M ratio calculated from the subject image is converted based on the conversion function thus calculated. Alternatively, a plurality of conversion functions may be calculated in advance and stored in the conversion function storage unit 17. Then, the H/M ratio conversion processing unit 29 may calculate the H/M ratio of the subject based on the stored conversion function. The plurality of conversion functions may be stored in the conversion function storage unit 17 through the IO device 4.

Figure 13:
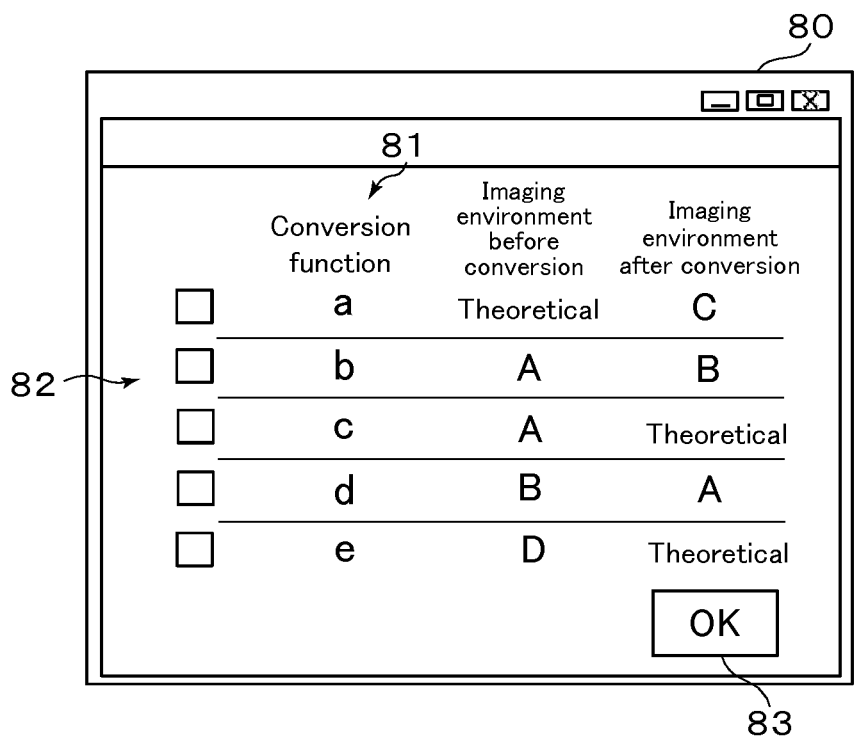
FIG. 13 illustrates a conversion function selection window 80 for selecting a conversion function.

FIG. 13 illustrates a conversion function selection window 80 that is displayed on the display of the output device 3 and is used for selecting the conversion function.

As illustrated in FIG. 13, the conversion function selection window 80 displays a list 81 of the conversion functions stored in the conversion function storage unit 17. The imaging environments before and after the conversion respectively corresponding to the conversion functions are displayed on the list 81. When the user checks a checkbox 82 of the conversion function he or she wants to use and presses an OK button 83, the conversion function to be used for calculating the H/M ratio is selected.

The conversion function thus selected is used in the conversion step (S39) of converting the H/M ratio obtained from the image of the subject captured in the first imaging environment as described with reference to FIG. 6. When a conversion function a for calculating the H/M ratio, obtained from an imaging environment C, from the theoretical H/M ratio is selected in FIG. 13, the H/M ratio conversion processing unit 29 may read out data on the conversion function a and convert the theoretical H/M ratio into the H/M ratio obtained from the imaging environment C. When a conversion function for converting the H/M ratio obtained from the first imaging environment into the H/M ratio obtained from the second imaging environment is selected, for example, as illustrated in FIG. 4, an H/M ratio (2.7) corresponding to the second imaging environment may be directly calculated from an H/M ratio (2.2) corresponding to the first imaging environment with the conversion function F1. Furthermore, as illustrated in FIG. 12, a theoretical H/M ratio (3.1) may be calculated from the H/M ratio (2.2) corresponding to the first imaging environment with the conversion function F2, and the H/M ratio (2.7) corresponding to the second imaging environment may be calculated from the theoretical H/M ratio (3.1) with the conversion function F3. When the H/M ratio obtained from a desired imaging environment is calculated via the theoretical H/M ratio as in the latter case, only the conversion function for converting between H/M ratios obtained from a certain imaging environment and the theoretical H/M ratio needs to be stored. Thus, the conversion function can be more simply associated with each other and can be managed more easily.

In the H/M ratio conversion processing illustrated in FIG. 6, the theoretical H/M ratio of the subject may be converted into the H/M ratio of the subject in the first imaging environment by using a function for converting the theoretical H/M ratio into the H/M ratio obtained from the first imaging environment. In this case, the theoretical H/M ratio of the subject is stored in step S31, and step S39 is executed without executing steps S35 and S37.

The conversion function stored in the conversion function storage unit 17 is used. Alternatively, a plurality of conversion functions stored in the server connected through the network may be recognized and displayed on the list 81 in the conversion function selection window 80. Then, the selected conversion function may be acquired from the server.

Figure 14:
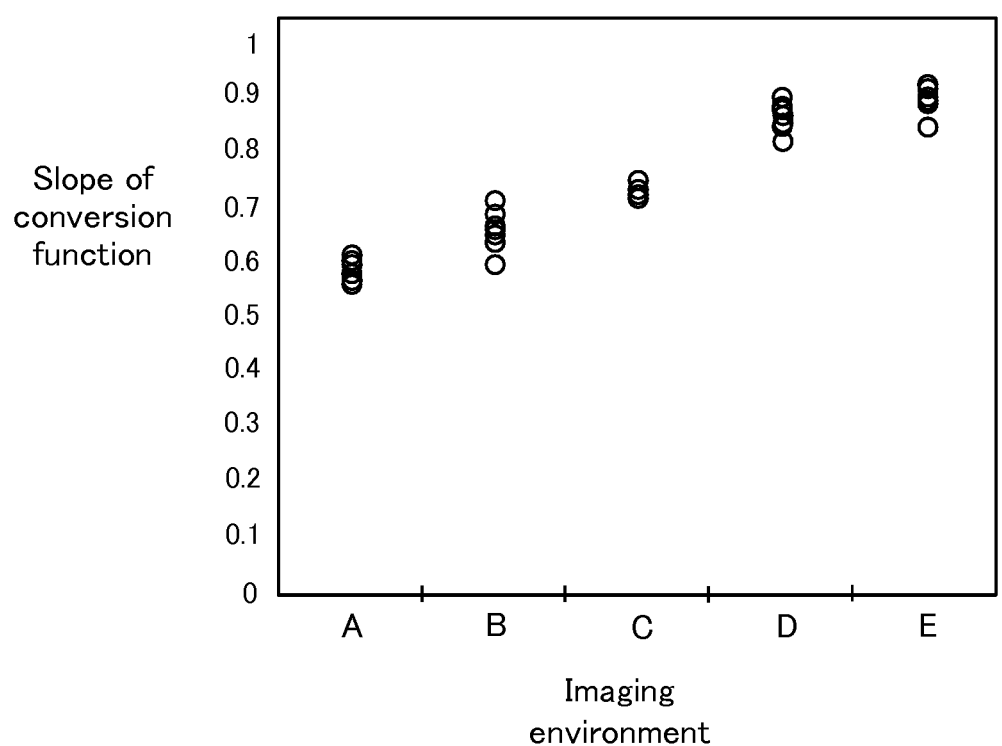
FIG. 14 is an explanatory diagram illustrating fluctuation of slopes of conversion functions.

FIG. 14 is an explanatory diagram illustrating levels of fluctuation of a slope of the conversion function for converting the theoretical H/M ratio into the H/M ratio obtained from each imaging environment.

When the H/M ratios are calculated by capturing images of the phantom for a plurality of times in a predetermined imaging environment and under imaging conditions, the resultant H/M ratios fluctuate. Thus, when the conversion function is calculated for a plurality of times, the slope of the conversion function as a linear function fluctuates as illustrated in FIG. 14. An average value is calculated by a plurality of the slopes, and can use for the conversion function. Thus, a more accurate conversion function can be obtained. Furthermore, a median or a mode of the slopes may be used instead of the average value.

The conversion function may be calculated by calculating and using an average value of the H/M ratios obtained under the imaging conditions in a predetermined imaging environment. Alternatively, the median or the mode of a plurality of H/M ratios may be used instead of the average value of the plurality of H/M ratios.

In the second embodiment described above, the index related to the 5 year mortality risk is calculated as the index indicating the probability of an occurrence of the predetermined event. Alternatively, the predetermined event may be a mortality risk of any years, or the predetermined event may be fatal arrhythmia or sudden cardiac death, rather than.

The NYHA class as the independent variable has four classes I to IV. Alternatively, the regression analysis may be performed with the NYHA class as two categories with one including the classes I and II and the other one including the classes III and IV. Furthermore, the regression analysis may be performed with every ten years of age being a single category.

In the embodiments described above, the processing of calculating the H/M ratio and the processing of calculating the 5 year mortality risk are separately executed. Alternatively, the processing of calculating 5 year mortality risk function may be performed in advance before being combined with the processing of calculating the H/M ratio, so that the 5 year mortality risk is calculated when the H/M ratio is calculated.

The subject data may include at least one of the H/M ratio, the age and the gender of the subject, the index indicating the severity of the heart failure, and the index indicating the left ventricular function. In the embodiments described above, five independent variables, including the H/M ratio, the age and the gender of the subject, the index indicating the severity of the heart failure, and the index indicating the left ventricular function, are used in the function related to the 5 year mortality risk. Alternatively, the H/M ratio may be the only independent variable. Furthermore, the H/M ratio and at least one of the age, the gender, the index indicating the severity of the heart failure, and the index indicating the left ventricular function of the subject may be used in the function.

In the 5 year mortality risk calculation processing in FIG. 9, the subject data stored in the subject data storage unit 113 is acquired in step S53. Alternatively, the 5 year mortality risk may be calculated by acquiring the subject data input to a data input window 90 as illustrated in FIG. 15(A).

FIG. 15(A) illustrates the data input window 90 that is displayed on the display of the output device 3 and is used for inputting the subject data.

As illustrated in FIG. 15(A), the data input window 90 includes a subject data input area 91, a Calc button 92, a 5 year mortality risk display portion 93, and a correction checkbox 94. The age, the NYHA class, the H/M ratio, the gender, and the LVEF of the subject as the subject data can be input to the subject data input area 91.

When the user clicks the Calc button 92 after inputting the subject data, the 5 year mortality risk is calculated based on the input subject data and the 5 year mortality risk function stored in the mortality risk function storage unit 115, and the 5 year mortality risk thus calculated is displayed on the 5 year mortality risk display portion 93.

When the correction checkbox 94 is checked as illustrated in FIG. 15(B), the H/M ratio that has been input is corrected by the H/M ratio in a predetermined imaging environment, and then the 5 year mortality risk is calculated. The correction is executed by storing the conversion function for converting the imaging environment corresponding to the H/M ratio that has been input into the predetermined imaging environment or the conversion function for converting the imaging environment corresponding to the H/M ratio that has been input into the theoretical H/M ratio and the conversion function for converting the theoretical H/M ratio into the predetermined imaging environment, and reading out and executing the conversion functions. Thus, with standardized imaging environment obtained from the predetermined imaging environment, the standardized 5 year mortality risk can be calculated. In the present embodiment, the 5 year mortality risk changes from 25% to 35% by correcting the H/M ratio, as illustrated in FIG. 15.

The embodiments described above can be expressed as follows.

An information processing system includes: a storage device that stores a first phantom Heart/Mediastinum ratio (H/M ratio) and a second phantom H/M ratio based on a phantom, the first phantom H/M ratio that is an H/M ratio of the phantom in the first imaging environment being acquired by performing, based on phantom data that is data of a first phantom image obtained by imaging the phantom in the first imaging environment and digital phantom data that is data of a digital phantom including a cardiac ROI and a mediastinum ROI, positioning of the digital phantom on the first phantom image, and by calculating based on the phantom data of the first phantom image to which the cardiac ROI and the mediastinum ROI are set; and a processor that acquires the first phantom H/M ratio and the second phantom H/M ratio stored in the storage device and calculate a conversion function based on the first phantom H/M ratio and the second phantom H/M ratio.

In the information processing system, the second phantom H/M ratio that is an H/M ratio of the phantom in a second imaging environment is acquired by performing, based on phantom data that is data of a second phantom image obtained by imaging the phantom in the second environment and the digital phantom data, positioning of the digital phantom on the second phantom image, and by calculating based on the phantom data on the second phantom image to which the cardiac ROI and the mediastinum ROI are set; and the conversion function is a function for converting the first phantom H/M ratio into the second phantom H/M ratio.

In the information processing system, the phantom data is data on the first phantom image as an image of the phantom captured under a predetermined imaging condition in the first imaging environment, the second phantom H/M ratio is an H/M ratio that is obtained under the predetermined imaging condition and is independent from the imaging environments, and the conversion function is a function with which conversion between the first phantom H/M ratio and the H/M ratio independent from the imaging environments is achievable.

An information processing system includes: a storage device that stores a conversion function obtained based on a first phantom Heart/Mediastinum ratio (H/M ratio) and a second phantom H/M ratio based on a phantom, the first phantom H/M ratio that is an H/M ratio of the phantom in the first imaging environment being acquired by performing, based on phantom data that is data of a first phantom image obtained by imaging the phantom in the first imaging environment and digital phantom data that is data of a digital phantom including a cardiac ROI and a mediastinum ROI, positioning of the digital phantom on the first phantom image, and by calculating based on the phantom data of the first phantom image to which the cardiac ROI and the mediastinum ROI are set; and a processor that acquires the conversion function from the storage device and convert an H/M ratio related to a subject by using the conversion function.

In the information processing system, the second phantom H/M ratio is an H/M ratio of the phantom in a second imaging environment is acquired by performing, based on phantom data that is data of a second phantom image obtained by imaging the phantom in the second environment and the digital phantom data, positioning of the digital phantom on the second phantom image, and by calculating based on the phantom data on the second phantom image to which the cardiac ROI and the mediastinum ROI are set; the conversion function is a function for converting the first phantom H/M ratio into the second phantom H/M ratio; and the H/M ratio related to the subject is an H/M ratio of the subject in the first imaging environment.

In the information processing system, the phantom data is data on the first phantom image obtained by imaging the phantom in a predetermined imaging condition of the first imaging environment, the second phantom H/M ratio is an H/M ratio that is obtained under the predetermined imaging condition and is independent from the imaging environments, the conversion function is a function with which conversion between the first phantom H/M ratio and the H/M ratio independent from the imaging environments is achievable, with the conversion function, the processor converts the H/M ratio related to the subject into the H/M ratio of the subject independent from the imaging environments, or converts the H/M ratio of the subject independent from the imaging environments into the H/M ratio related to the subject, and the H/M ratio related to the subject is an H/M ratio of the subject in the first imaging environment.

REFERENCE SIGNS LIST 1 information processing apparatus
5 Phantom
10 Information processing apparatus main body
11 Phantom image data storage unit
13 Digital phantom data storage unit
15 H/M ratio data storage unit
17 Conversion function storage unit
19 Subject image data storage unit
21 Positioning processing unit
23 ROI setting unit
25 H/M ratio calculation unit
27 Conversion function calculation unit
29 H/M ratio conversion processing unit

The invention claimed is:

1. A non-transitory computer-readable storage medium storing a program causing a computer to execute processing of:
positioning a digital phantom on a first phantom image based on phantom data that is data of the first phantom image obtained by imaging a phantom in a first imaging environment and digital phantom data that is data of the digital phantom including a cardiac ROI and a mediastinum ROI;
setting the cardiac ROI and the mediastinum ROI to the first phantom image on which the digital phantom is positioned;
calculating a first phantom Heart/Mediastinum ratio (H/M ratio) that is an H/M ratio of the phantom in the first imaging environment, based on the phantom data of the first phantom image to which the cardiac ROI and the mediastinum ROI are set;
acquiring a second phantom Heart/Mediastinum ratio (H/M ratio) based on the phantom; and
calculating a conversion function based on the first phantom H/M ratio and the second phantom H/M ratio.

2. The storage medium according to claim 1, wherein the second phantom H/M ratio that is an H/M ratio of the phantom in a second imaging environment is acquired by performing, based on phantom data that is data of a second phantom image obtained by imaging the phantom in the second environment and the digital phantom data, positioning of the digital phantom on the second phantom image, and by calculating based on the phantom data on the second phantom image to which the cardiac ROI and the mediastinum ROI are set; and
the conversion function is a function converting the first phantom H/M ratio into the second phantom H/M ratio.

3. The storage medium according to claim 2, wherein the first phantom H/M ratio is any one of an average value, a median value, and a mode value of a plurality of H/M ratios, corresponding to each imaging condition of the phantom in the first imaging environment, calculated based on a plurality of the first phantom images by capturing for a plurality of times an image of the phantom in the first imaging environment according to each imaging condition, and
the second phantom H/M ratio is any one of an average value, a median value, and a mode value of a plurality of H/M ratios, corresponding to each imaging condition of the phantom in the second imaging environment, calculated based on a plurality of the second phantom images by capturing for a plurality of times an image of the phantom in the second imaging environment according to each imaging condition.

4. The storage medium according to claim 2, wherein the conversion function includes:
a first conversion function converting the first phantom H/M ratio into an H/M ratio independent from the imaging environments; and
a second conversion function converting the H/M ratio independent from the imaging environments into the second phantom H/M ratio.

5. The storage medium according to claim 1, wherein the phantom data is data of the first phantom image obtained by imaging the phantom in a predetermined imaging condition of the first imaging environment,
the second phantom H/M ratio is an H/M ratio that is obtained under the predetermined imaging condition and is independent from the imaging environments, and
the conversion function is a function converting the first phantom H/M ratio into the H/M ratio independent from the imaging environments or converting the H/M ratio independent from the imaging environments into the first phantom H/M ratio.

6. The storage medium according to claim 5, wherein the first phantom H/M ratio is any one of an average value, a median value, and a mode value of a plurality of H/M ratios, corresponding to each imaging condition of the phantom in the first imaging environment, calculated based on a plurality of the first phantom images by capturing for a plurality of times an image of the phantom in the first imaging environment in accordance with each imaging condition.

7. A non-transitory computer-readable storage medium storing a program causing a computer to execute processing of:
  setting a cardiac ROI and a mediastinum ROI in a subject image obtained by imaging of a subject in a first imaging environment;
  calculating an H/M ratio related to the subject based on the subject image to which the cardiac ROI and the mediastinum ROI are set;
  acquiring a conversion function obtained based on a first phantom Heart/Mediastinum ratio (H/M ratio) and a second phantom H/M ratio based on a phantom, the first phantom H/M ratio that is an H/M ratio of the phantom in the first imaging environment being calculated based on phantom data of a first phantom image to which a cardiac ROI and a mediastinum ROI are set, with a digital phantom including the cardiac ROI and the mediastinum ROI being positioned on the first phantom image based on the phantom data that is data of the first phantom image obtained by imaging the phantom in the first imaging environment and digital phantom data that is data of the digital phantom; and
  converting the H/M ratio related to the subject obtained from the first imaging environment into an H/M ratio of the second imaging environment by using the conversion function.

8. The storage medium according to claim 7, wherein the conversion function is a linear function with a slope, and the slope is any one of an average value, a median value, and a mode value of a plurality of the slopes as a result of obtaining the conversion function for a plurality of times.

9. The storage medium according to claim 7, wherein the second phantom H/M ratio is an H/M ratio of the phantom in a second imaging environment is acquired by performing, based on phantom data that is data of a second phantom image obtained by imaging the phantom in the second environment and the digital phantom data, positioning of the digital phantom on the second phantom image, and by calculating based on the phantom data on the second phantom image to which the cardiac ROI and the mediastinum ROI are set;
the conversion function is a function converting the first phantom H/M ratio into the second phantom H/M ratio; and
the H/M ratio related to the subject is an H/M ratio of the subject in the first imaging environment.

10. The storage medium according to claim 9, wherein the conversion function includes:
  a first conversion function converting the first phantom H/M ratio into an H/M ratio independent from the imaging environments; and
  a second conversion function converting the H/M ratio independent from the imaging environments into the second phantom H/M ratio.

11. The storage medium according to claim 7, wherein the phantom data is data on the first phantom image obtained by imaging the phantom in a predetermined imaging condition of the first imaging environment,
the second phantom H/M ratio is an H/M ratio that is obtained under the predetermined imaging condition and is independent from the imaging environments,
the conversion function is a function converting the first phantom H/M ratio into the H/M ratio independent from the imaging environments or converting the H/M ratio independent from the imaging environments into the first phantom H/M ratio, in use of the conversion function, the H/M ratio related to the subject is converted into the H/M ratio of the subject independent from the imaging environments, or the H/M ratio of the subject independent from the imaging environments is converted into the H/M ratio related to the subject, and
the H/M ratio related to the subject is an H/M ratio of the subject in the first imaging environment.

12. An information processing apparatus comprising:
  a processor; and
  a memory containing instructions that, when executed by the processor, cause the processor to:
    position a digital phantom on a first phantom image based on phantom data that is data of the first phantom image obtained by imaging a phantom in a first imaging environment and digital phantom data that is data of the digital phantom including a cardiac ROI and a mediastinum ROI;
    set the cardiac ROI and the mediastinum ROI to the first phantom image on which the digital phantom is positioned;
    calculate a first phantom Heart/Mediastinum ratio (H/M ratio) that is an H/M ratio of the phantom in the first imaging environment, based on the phantom data of the first phantom image to which the cardiac ROI and the mediastinum ROI are set;
    acquire a second phantom Heart/Mediastinum ratio (H/M ratio) based on the phantom; and
    calculate a conversion function based on the first phantom H/M ratio and the second phantom H/M ratio.

13. The information processing apparatus according to claim 12, wherein
the second phantom H/M ratio is an H/M ratio of the phantom in a second imaging environment is acquired by performing, based on phantom data that is data of a second phantom image obtained by imaging the phantom in the second environment and the digital phantom data, positioning of the digital phantom on the second phantom image, and by calculating based on the phantom data on the second phantom image to which the cardiac ROI and the mediastinum ROI are set; and
the conversion function is a function converting the first phantom H/M ratio into the second phantom H/M ratio.

14. The information processing apparatus according to claim 13, wherein
the first phantom H/M ratio is any one of an average value, a median value, and a mode value of a plurality of H/M ratios, corresponding to each imaging condition of the phantom in the first imaging environment, calculated based on a plurality of the first phantom images by capturing for a plurality of times an image of the phantom in the first imaging environment according to each imaging condition, and
the second phantom H/M ratio is any one of an average value, a median value, and a mode value of a plurality of H/M ratios, corresponding to each imaging condition of the phantom in the second imaging environment, calculated based on a plurality of the second phantom images by capturing for a plurality of times an image of the phantom in the second imaging environment according to each imaging condition.

15. The information processing apparatus according to claim 12, wherein
the phantom data is data on the first phantom image obtained by imaging the phantom in a predetermined imaging condition of the first imaging environment,
the second phantom H/M ratio is an H/M ratio that is obtained under the predetermined imaging condition and is independent from the imaging environments, and
the conversion function is a function with which conversion between the first phantom H/M ratio and the H/M ratio independent from the imaging environments is achievable.

16. The information processing apparatus according to claim 15, wherein the first phantom H/M ratio is any one of an average value, a median value, and a mode value of a plurality of H/M ratios, corresponding to each imaging condition of the phantom in the first imaging environment calculated based on a plurality of the first phantom images by capturing for a plurality of times an image of the phantom in the first imaging environment in accordance with each imaging condition.

17. An information processing apparatus comprising:
a processor; and
a memory containing instructions that, when executed by the processor, cause the processor to:
set a cardiac ROI and a mediastinum ROI in a subject image obtained by imaging of a subject in a first imaging environment;
calculate an H/M ratio related to the subject based on the subject image to which the cardiac ROI and the mediastinum ROI are set;
acquire a conversion function obtained based on a first phantom Heart/Mediastinum ratio (H/M ratio) and a second phantom H/M ratio based on a phantom, the first phantom H/M ratio that is an H/M ratio of the phantom in the first imaging environment being calculated based on phantom data of a first phantom image to which a cardiac ROI and a mediastinum ROI are set, with a digital phantom including the cardiac ROI and the mediastinum ROI being positioned on the first phantom image based on the phantom data that is data of the first phantom image obtained by imaging the phantom in the first imaging environment and digital phantom data that is data of the digital phantom; and
convert the H/M ratio related to the subject obtained from the first imaging environment into an H/M ratio of the second imaging environment by using the conversion function.

18. The information processing apparatus according to claim 17, wherein the conversion function is a linear function with a slope, and the slope is any one of an average value, a median value, and a mode value of a plurality of the slopes as a result of obtaining the conversion function for a plurality of times.

19. The information processing apparatus according to claim 17, wherein
the second phantom H/M ratio is an H/M ratio of the phantom in a second imaging environment is acquired by performing, based on phantom data that is data of a second phantom image obtained by imaging the phantom in the second environment and the digital phantom data, positioning of the digital phantom on the second phantom image, and by calculating based on the phantom data on the second phantom image to which the cardiac ROI and the mediastinum ROI are set,
the conversion function is a function converting the first phantom H/M ratio into the second phantom H/M ratio, and
the H/M ratio related to the subject is an H/M ratio of the subject in the first imaging environment.

20. The information processing apparatus according to claim 17, wherein
the phantom data is data on the first phantom image obtained by imaging the phantom in a predetermined imaging condition of the first imaging environment,
the second phantom H/M ratio is an H/M ratio that is obtained under the predetermined imaging condition and is independent from the imaging environments,
the conversion function is a function with which conversion between the first phantom H/M ratio and the H/M ratio independent from the imaging environments is achievable,
in use of the conversion function, the conversion unit converts the H/M ratio related to the subject into the H/M ratio of the subject independent from the imaging environments, or converts
the H/M ratio of the subject independent from the imaging environments into the H/M ratio related to the subject, and
the H/M ratio related to the subject is an H/M ratio of the subject in the first imaging environment.

* * * * *